US012521550B2

(12) United States Patent
Schepis et al.

(10) Patent No.: US 12,521,550 B2
(45) **Date of Patent: *Jan. 13, 2026**

(54) TUNABLE ELECTRICAL NOISE SIGNAL TECHNOLOGIES

(71) Applicant: Soin Neuroscience, LLC, Dayton, OH (US)

(72) Inventors: Eric A. Schepis, Alpharetta, GA (US); Amol Soin, Dayton, OH (US)

(73) Assignee: Soin Neuroscience, LLC, Dayton, OH (US)

( * ) Notice: Subject to any disclaimer, the term of this patent is extended or adjusted under 35 U.S.C. 154(b) by 190 days.

This patent is subject to a terminal disclaimer.

(21) Appl. No.: 18/473,533

(22) Filed: Sep. 25, 2023

(65) Prior Publication Data

US 2024/0157127 A1 May 16, 2024

Related U.S. Application Data

(63) Continuation of application No. 17/545,031, filed on Dec. 8, 2021, now Pat. No. 11,766,559, which is a (Continued)

(51) Int. Cl.

*A61N 1/05* (2006.01)
*A61N 1/36* (2006.01)

(52) U.S. Cl.

CPC ........... *A61N 1/0529* (2013.01); *A61N 1/056* (2013.01); *A61N 1/36071* (2013.01)

(58) Field of Classification Search

CPC ... A61N 1/0529; A61N 1/056; A61N 1/36071
See application file for complete search history.

(56) References Cited

U.S. PATENT DOCUMENTS

| | | | |
|---|---|---|---|
| 5,983,141 | A | 11/1999 | Sluijter et al. |
| 7,117,038 | B1 | 10/2006 | Overstreet |

(Continued)

FOREIGN PATENT DOCUMENTS

| | | | |
|---|---|---|---|
| EP | 2703042 A1 | 3/2014 | |
| JP | 2006204520 A | 8/2006 | |

(Continued)

OTHER PUBLICATIONS

International Search Report, European Patent Office, International Patent Application No. PCT/US2018/013700, Mar. 19, 2018, 4 pages.

(Continued)

*Primary Examiner* — Michael J Lau

(74) *Attorney, Agent, or Firm* — Taft Stettinius & Hollister LLP

(57) ABSTRACT

A method of providing therapy to a patient according to one embodiment includes generating an electrical noise signal by at least one noise generator controlled by a controller of a tunable noise system, partitioning the electrical noise signal into a plurality of discrete frequency bands, each of the discrete frequency bands having a corresponding bandwidth, delivering the electrical noise signal through one or more electrodes to the patient to target at least one of neural tissue or non-neural tissue of the patient, adjusting an amplitude of one or more of a voltage or current of the electrical noise signal within a selected frequency band of the plurality of discrete frequency bands to generate an adjusted electrical signal based on feedback received from the patient, and delivering the adjusted electrical signal through the one or more electrodes to provide therapy to the patient.

20 Claims, 22 Drawing Sheets

Related U.S. Application Data continuation-in-part of application No. 16/478,381, filed as application No. PCT/US2018/013700 on Jan. 15, 2018, now abandoned.

(60) Provisional application No. 62/447,504, filed on Jan. 18, 2017.

(56) References Cited

U.S. PATENT DOCUMENTS

| | | | | |
|---|---|---|---|---|
| 11,766,559 | B2 * | 9/2023 | Schepis | A61N 1/36071 607/46 |
| 2003/0114886 | A1 | 6/2003 | Gluckman et al. | |
| 2006/0149337 | A1 * | 7/2006 | John | A61N 1/37235 607/45 |
| 2007/0142864 | A1 | 6/2007 | Libbus et al. | |
| 2007/0142874 | A1 * | 6/2007 | John | A61N 2/006 607/45 |
| 2008/0077192 | A1 * | 3/2008 | Harry | A61N 1/0476 42/84 |
| 2008/0269836 | A1 | 10/2008 | Foffani et al. | |
| 2010/0010556 | A1 | 1/2010 | Zhao et al. | |
| 2011/0009919 | A1 | 1/2011 | Carbunaru et al. | |
| 2011/0009923 | A1 | 1/2011 | Lee | |
| 2011/0201944 | A1 * | 8/2011 | Higgins | A61N 1/37258 607/45 |
| 2012/0059438 | A1 | 3/2012 | De Ridder | |
| 2012/0123502 | A1 | 5/2012 | Aghassian et al. | |
| 2013/0245486 | A1 * | 9/2013 | Simon | A61B 5/4836 607/46 |
| 2013/0253365 | A1 | 9/2013 | Crosson et al. | |
| 2013/0317564 | A1 | 11/2013 | Lin et al. | |
| 2014/0031895 | A1 * | 1/2014 | Rahimi | A61N 1/36021 607/46 |
| 2014/0316268 | A1 | 10/2014 | Kafiluddi et al. | |
| 2015/0012063 | A1 | 1/2015 | Chen | |
| 2015/0157864 | A1 * | 6/2015 | Rosenberg | A61N 1/36171 607/62 |
| 2016/0199662 | A1 * | 7/2016 | Wundrich | A61N 1/0484 607/45 |
| 2016/0256689 | A1 | 9/2016 | Vallejo et al. | |
| 2016/0271413 | A1 * | 9/2016 | Vallejo | A61N 1/36196 |
| 2017/0001003 | A1 | 1/2017 | Pivonka et al. | |
| 2017/0001016 | A1 * | 1/2017 | De Ridder | A61N 1/36135 |

FOREIGN PATENT DOCUMENTS

| | | | |
|---|---|---|---|
| JP | 2009505689 | A | 2/2009 |
| WO | 9318821 | A1 | 9/1993 |

OTHER PUBLICATIONS

Written Opinion, European Patent Office, International Patent Application No. PCT/US2018/013700, Mar. 19, 2018, 7 pages.

Australian First Examination Report; Australia Patent Office; Australian Patent Application No. 2018210216; Aug. 23, 2019; 2 pages.

Canadian Office Action; Canadian Intellectual Property Office; Canadian Patent Application No. 3,048,498; Jan. 29, 2020; 5 pages.

Japanese Office Action; Japan Patent Office; Japanese Patent Application No. 2019-538339; Dec. 10, 2019; 14 pages.

Korean Office Action; Korean Intellectual Property Office; Korean Patent Application No. 10-2019-7023751; Nov. 14, 2019; 4 pages.

New Zealand First Examination Report; New Zealand Intellectual Property Office; New Zealand Patent Application No. 756351; Feb. 10, 2020; 3 pages.

* cited by examiner

TUNABLE ELECTRICAL NOISE SIGNAL TECHNOLOGIES

CROSS-REFERENCE TO RELATED APPLICATIONS

This application is a continuation of U.S. patent application Ser. No. 17/545,031, filed on Dec. 8, 2021, which is a continuation-in-part of U.S. patent application Ser. No. 16/478,381, filed on Jul. 16, 2019, which is a national stage entry of PCT Patent Application No. PCT/US2018/013700, filed on Jan. 15, 2018, which claims priority to U.S. Provisional Application No. 62/447,504, filed on Jan. 18, 2017, the contents of each of which are incorporated herein by reference in their entirety.

TECHNICAL FIELD

The technology described herein generally relates to providing therapy to a patient via the application of a tunable noise signal.

BACKGROUND

Periodic electrical waveforms are commonly used to stimulate nervous tissue to treat patients with neurological disorders. Fourier's theorem teaches that those periodic waveforms (i.e., pulses) are composed of sinusoidal signals that are harmonically related to the repetition frequency of the original signal. "Harmonically related" means that the frequency of the sinusoids is an integral multiple of some "basic" or "fundamental" number. That is, the frequency is one times, two times, three times, etc. the basic or fundamental number. Each of the component frequencies is known as a harmonic, and, collectively, these component frequencies are known as the Fourier series. The amplitude of each harmonic is correlated to the amplitude of the fundamental frequency.

Altogether, the electrical stimulation waveforms that are used today limit stimulation energy to the harmonic frequencies of the periodic signal, and do not deliver energy at frequencies between the harmonic frequencies or at frequencies that are less than the fundamental frequency. Moreover, they do not enable independent control of the energy content of any frequency within its spectrum. For example, periodic biphasic square-wave pulses are used to stimulate nervous tissue to treat pain, motor, and sensory disorders. The Fourier series of a biphasic square-wave pulse includes the fundamental frequency, and its odd multiples (i.e., it does not have even numbered harmonics). The amplitude of each harmonic is represented as 1/integral multiple of the fundamental frequency's (i.e., 1, 3, 5, 7, 9) amplitude. That is, constant-voltage biphasic square-wave pulses delivered at 200 Hertz (Hz) and 1 volt (V) has a fundamental frequency (amplitude) of 200 Hz (1/1 V) and harmonics at 600 Hz (⅓ V)), 1000 Hz (⅕ V), 1400 Hz (1/7 V), and 1800 Hz (1/9 V), etc. This stimulation waveform does not deliver energy at frequencies that are less than 200 Hz (fundamental frequency) or between harmonics (e.g., between 200 Hz and 600 Hz; between 600 Hz and 1000 Hz; between 1000 Hz and 1400 Hz, etc.), and the energy content delivered in each harmonic is fixed to that of the fundamental frequency and cannot be independently modulated (i.e., deliver 1 V at 1000 Hz and ⅓ Vat 200 Hz).

An electrical stimulation therapy that delivers a waveform that is flexible in both frequency and energy content at each frequency, would better accommodate for patient variability and disease state, ultimately leading to better patient outcomes. Moreover, a random waveform would help prevent neurological tolerance, which is a phenomenon that plagues long-term efficacy of periodic stimulation waveforms. Untuned electrical noise has been used previously to modulate neural tissues, but it has not been refined, adjusted, or modified to aptly affect neural and non-neural circuitry and treat disease. As such, there is an unmet need for a method and system for delivering a broad spectrum of electrical noise signals to neural tissue, non-neural tissue, or a combination thereof (e.g., tissue within or adjacent the brain, the spinal cord, a dorsal root ganglion, a sympathetic chain ganglion, a peripheral nerve, etc.) of a patient, where the electrical noise signals are tunable. A broad spectrum of electrical noise signals would enable improved modulation of the target neural tissue, non-neural tissue, or a combination thereof, and the tunability feature would account for disease and patient variability, where feedback from the patient could be used to tune or adjust the broad spectrum of electrical noise signals delivered to the patient.

SUMMARY

One embodiment is directed to a unique system and methods for providing therapy to a patient using tunable electrical noise signals. Other embodiments are directed to apparatuses, systems, devices, hardware, methods, and combinations thereof for providing therapy to a patient using tunable electrical noise signals.

According to an embodiment, a method for providing therapy to a patient includes delivering a broad spectrum of electrical noise signals to target neural tissue, non-neural tissue, or a combination thereof in the patient via an electrode, wherein the broad spectrum of electrical noise signals are tunable, and using feedback from the patient to tune the broad spectrum of electrical noise signals to optimize the therapy provided to the patient.

In some embodiments, the broad spectrum of electrical noise signals can be tuned by adjusting energy contained within a frequency band.

In some embodiments, the broad spectrum of electrical noise signals can be tuned by adjusting a phase component of the broad spectrum of electrical signals.

In some embodiments, the therapy provided to the patient can treat pain.

In some embodiments, the therapy provided to the patient can treat an autonomic disorder.

In some embodiments, the therapy provided to the patient can treat a sensory disorder.

In some embodiments, the therapy provided to the patient can treat a motor disorder.

In some embodiments, the therapy provided to the patient can elicit plastic changes in neural tissue, non-neural tissue, or a combination thereof to mitigate or abolish a pathophysiologic disease or syndrome.

In some embodiments, the target neural tissue, non-neural tissue, or a combination thereof can be tissue located within or adjacent the patient's brain, the patient's spinal cord, a dorsal root ganglion, a sympathetic chain ganglion, or a peripheral nerve.

In some embodiments, the electrode can be percutaneous, transcutaneous, or implantable.

In some embodiments, the electrode can be coupled to a noise generator and a controller, the noise generator can be implantable or the noise generator can be positioned external to the patient, and the controller can be configured to tune the broad spectrum of electrical noise signals.

In some embodiments, the broad spectrum of electrical noise signals can include Gaussian noise, white noise, pink noise, Brownian noise, grey noise, or a combination thereof.

In some embodiments, only tuned electrical noise signals are delivered to the target neural tissue, non-neural tissue, or a combination thereof.

According to another embodiment, a system for providing therapy to a patient includes an electrode, a noise generator coupled to the electrode, and a controller, wherein the controller instructs the noise generator to deliver a broad spectrum of electrical noise signals to target neural tissue, non-neural tissue, or a combination thereof via the electrode, wherein the broad spectrum of electrical noise signals are tunable, and wherein the controller is configured to tune the broad spectrum of electrical noise signals to optimize the therapy provided to the patient based on feedback received from the patient.

In some embodiments, the controller can tune the broad spectrum of electrical noise signals by adjusting energy contained within a frequency band.

In some embodiments, the controller can tune the broad spectrum of electrical noise signals by adjusting a phase component of the broad spectrum of electrical signals.

In some embodiments, the therapy provided to the patient can treat pain.

In some embodiments, the therapy provided to the patient can treat an autonomic disorder.

In some embodiments, the therapy provided to the patient can treat a sensory disorder.

In some embodiments, the therapy provided to the patient can treat a motor disorder.

In some embodiments, the therapy provided to the patient can elicit plastic changes in neural tissue, non-neural tissue, or a combination thereof to mitigate or abolish a pathophysiologic disease or syndrome.

In some embodiments, the target neural tissue, non-neural tissue, or a combination thereof can be located within or adjacent the patient's brain, the patient's spinal cord, a dorsal root ganglion, a sympathetic chain ganglion, or a peripheral nerve.

In some embodiments, the electrode can be percutaneous, transcutaneous, or implantable.

In some embodiments, the noise generator can be implantable, or the noise generator can be positioned external to the patient.

In some embodiments, the broad spectrum of electrical noise signals can include Gaussian noise, white noise, pink noise, Brownian noise, grey noise, or a combination thereof.

In some embodiments, only tuned electrical noise signals can be delivered to the target neural tissue, non-neural tissue, or a combination thereof.

According to yet another embodiment, a method for providing therapy to a patient may include generating an electrical noise signal by at least one noise generator controlled by a controller of a tunable noise system, partitioning the electrical noise signal into a plurality of discrete frequency bands, each of the discrete frequency bands having a corresponding bandwidth, delivering the electrical noise signal through one or more electrodes to the patient to target at least one of neural tissue or non-neural tissue of the patient, adjusting an amplitude of one or more of a voltage or current of the electrical noise signal within a selected frequency band of the plurality of discrete frequency bands to generate an adjusted electrical signal based on feedback received from the patient, and delivering the adjusted electrical signal through the one or more electrodes to provide therapy to the patient.

In some embodiments, the feedback received from the patient may be patient self-report regarding the therapy delivered to the patient.

In some embodiments, the feedback may be based on data generated by one or more sensors of the tunable noise system, wherein the one or more sensors measure one or more physiological outcomes of the patient.

In some embodiments, the feedback may include data received from a machine learning system.

In some embodiments, the method may further include executing the machine learning algorithm to identify a tuned electrical noise signal to be delivered through the one or more electrodes to provide therapy to the patient based on a plurality of machine learning inputs.

In some embodiments, the machine learning inputs may include one or more of tuned noise signatures, patient information, patient demographics, diagnosis information, electrode positioning, patient sensations, measures of treatment efficacy and/or outcomes, time of day, duration of treatment, or time elapsed since start of treatment plan.

In some embodiments, the method may further include delivering the tuned electrical noise signal through the one or more electrodes to provide therapy to the patient.

In some embodiments, the at least one noise generator may consist of a single noise generator.

In some embodiments, the at least one noise generator may include a plurality of noise generators, generating the electrical noise signal by the at least one noise generator may include generating a corresponding electrical noise signal with each noise generator of the plurality of noise generators, and each noise generator of the plurality of noise generators may correspond with a separate frequency band of the plurality of discrete frequency bands.

In some embodiments, the electrical noise signal may be or include at least one of Gaussian noise, white noise, pink noise, Brownian noise, or grey noise.

In some embodiments, adjusting the amplitude of the one or more of the voltage or current of the electrical noise signal within the selected frequency band may include amplifying the amplitude of the one or more of the voltage or current of the electrical noise signal within the selected frequency band.

In some embodiments, adjusting the amplitude of the one or more of the voltage or current of the electrical noise signal within the selected frequency band may include attenuating the amplitude of the one or more of the voltage or current of the electrical noise signal within the selected frequency band.

In some embodiments, adjusting the amplitude of the one or more of the voltage or current of the electrical noise signal within the selected frequency band may include adjusting the amplitude of the one or more of the voltage or current of the electrical noise signal within a first frequency band of the plurality of discrete frequency bands to generate a first adjusted electrical signal based on first feedback received from the patient, and the method may further include adjusting an amplitude of the one or more of the voltage or current of the adjusted electrical signal within a second frequency band of the plurality of discrete frequency bands to generate a second adjusted electrical signal based on second feedback received from the patient.

In some embodiments, the method may further include placing the one or more electrodes on the patient percutaneously or transcutaneously.

In some embodiments, at least one of the one or more electrodes may be implantable.

In some embodiments, each of the discrete frequency bands may have the same bandwidth.

In some embodiments, each of the discrete frequency bands in a frequency range of 0 Hz to 100 kHz of the partitioned electrical noise signal may have a bandwidth of one of 1 kHz or 2 k Hz.

In some embodiments, each of the discrete frequency bands may be an octave band.

In some embodiments, each of the octave bands may be one of a base-2 octave band or a base-10 octave band.

In some embodiment, the electrical noise signal may have a frequency range of 0 Hz to 100 kHz.

According to another embodiment, a method for providing therapy to a patient may include generating an electrical noise signal by a noise generator controlled by a controller of a tunable noise system, partitioning the electrical noise signal into a plurality of discrete frequency bands, each of the discrete frequency bands having a corresponding bandwidth, delivering the electrical noise signal through one or more electrodes to the patient to target at least one of neural tissue or non-neural tissue of the patient, adjusting a corresponding amplitude of one or more of the voltage or current of the electrical noise signal within a corresponding frequency band of the plurality of discrete frequency bands to generate an adjusted electrical signal based on feedback received from the patient for each of a plurality of selected frequency bands of the plurality of discrete frequency bands, and delivering the adjusted electrical signal through the one or more electrodes to provide therapy to the patient.

In some embodiments, the feedback may include at least one of feedback received from the patient as patient self-report regarding the therapy delivered to the patient, feedback based on data generated by one or more sensors of the tunable noise system, wherein the one or more sensors measure one or more physiological outcomes of the patient, or feedback data received from a machine learning system.

In some embodiments, the electrical noise signal may be or include at least one of Gaussian noise, white noise, pink noise, Brownian noise, or grey noise.

According to yet another embodiment, a system for providing therapy to a patient may include an electrode, a noise generator coupled to the electrode, and a controller. The controller may instruct the noise generator to deliver an electrical noise signal to target neural tissue, non-neural tissue, or a combination thereof via the electrode, wherein the electrical noise signal includes a plurality of discrete frequency bands that are tunable, wherein the controller is configured to tune an amplitude of one or more of the voltage or current of the electrical noise signal within each of the plurality of discrete frequency bands to optimize the therapy provided to the patient based on feedback received from the patient.

In some embodiments, to tune the amplitude of the one or more of the voltage or current of the electrical noise signal within each of the plurality of discrete frequency bands may include to independently amplify or attenuate the amplitude of the one or more of the voltage or current of the electrical noise signal within each of the plurality of discrete frequency bands.

This summary is not intended to identify key or essential features of the claimed subject matter, nor is it intended to be used as an aid in limiting the scope of the claimed subject matter. Further embodiments, forms, features, and aspects of the present application shall become apparent from the description and figures provided herewith.

BRIEF DESCRIPTION OF THE DRAWINGS

The concepts described herein are illustrative by way of example and not by way of limitation in the accompanying figures. For simplicity and clarity of illustration, elements illustrated in the figures are not necessarily drawn to scale. Where considered appropriate, references labels have been repeated among the figures to indicate corresponding or analogous elements.

DETAILED DESCRIPTION

Figure 1:
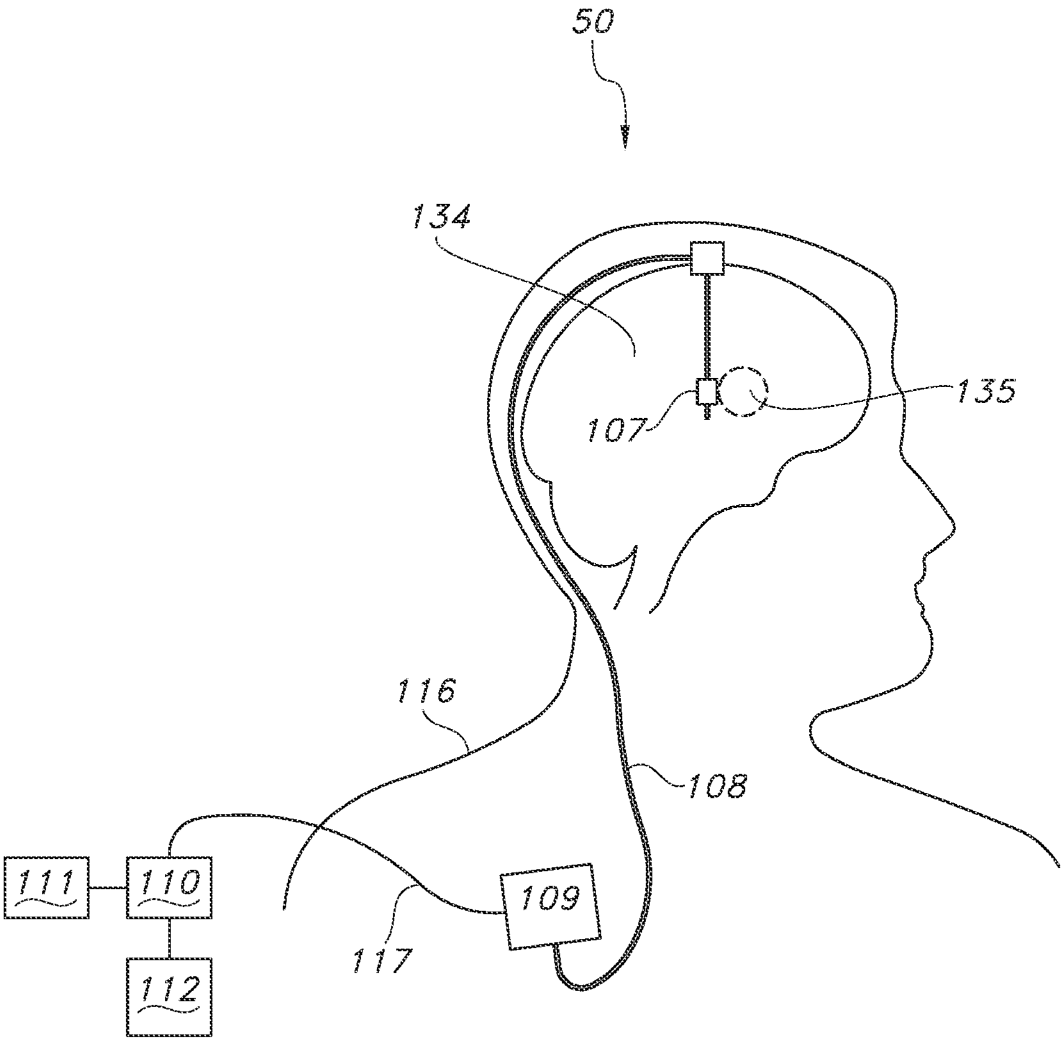
FIG. 1 illustrates at least one embodiment of a system for delivering a broad spectrum of electrical noise signals to target neural tissue, non-neural tissue, or a combination thereof in a patient, where the electrical noise signals are tunable, and where the target tissue is located within or adjacent to the patient's brain.

Although the concepts of the present disclosure are susceptible to various modifications and alternative forms, specific embodiments have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should further be appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described. Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Further, with respect to the claims, the use of words and phrases such as "a," "an," "at least one," and/or "at least one portion" should not be interpreted so as to be limiting to only one such element unless specifically stated to the contrary, and the use of phrases such as "at least a portion" and/or "a portion" should be interpreted as encompassing both embodiments including only a portion of such element and embodiments including the entirety of such element unless specifically stated to the contrary.

As used herein, the term "electrical noise signal" refers to a random electrical signal that can be applied to target neural tissue, non-neural tissue, or a combination thereof. The electrical noise signal can include Gaussian noise, white noise, pink noise, red (Brownian) noise, grey noise, or a multifaceted noise containing a combination of these and any other suitable noise signals as discussed in more detail below. The electrical noise signal can be band limited to an upper cutoff frequency and a lower cutoff frequency that are broader than the natural resonant frequencies of the modulated neuronal circuitry and electrical stimulation paradigms practiced today. Further, the electrical noise signal is distinguished from a traditional electrical stimulation signal in that it is a random signal that varies in an unpredictable manner over time, or is aperiodic. It should be further appreciated that the randomness of the electrical noise signal described herein is not dependent on external stimuli (e.g., kinetics, kinematics, or mechanics) or time. Traditional electrical stimulation signals are periodic waveforms that are predictable. A periodic waveform is not utilized in the electrical noise signal of the technologies described herein. In other words, the electrical noise signal is aperiodic, and unlike periodic signals used for stimulation today, the tuned electrical noise signal enables independent adjustment of the energy content within all frequencies of its frequency spectrum, for example, as described in further detail below. As such, the power spectrum of the tuned electrical noise signal may have one or more local maxima and/or one or more local minima. Local maxima may be in neighboring bandwidths or separated by one or more frequency bands. Similarly, local minima may be in neighboring bandwidths or separated by one or more frequency bands. The electrical power described as local maxima and local minima may interact and cause more effective, safer, and power efficient therapies.

The disclosed embodiments may, in some cases, be implemented in hardware, firmware, software, or a combination thereof. The disclosed embodiments may also be implemented as instructions carried by or stored on one or more transitory or non-transitory machine-readable (e.g., computer-readable) storage media, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures unless indicated to the contrary. Additionally, the inclusion of a structural or method feature in a particular figure is not meant to imply that such feature is required in all embodiments and, in some embodiments, may not be included or may be combined with other features.

Generally speaking, the technology described herein is directed to a method and system for providing therapy to a patient via delivery of a broad spectrum of tunable electrical noise signals. For example, a method includes delivering a broad spectrum of tunable electrical noise signals to target neural tissue, non-neural tissue, or a combination thereof in the patient via an electrode, and using feedback from the patient to tune the broad spectrum of electrical noise signals to optimize the therapy provided to the patient. A system includes an electrode, a noise generator coupled to the electrode, and a controller. Further, in some embodiments, the system may additionally include sensors for recording physiological outcomes as described herein. In the illustrative embodiment, the controller instructs the noise generator to deliver a broad spectrum of tunable electrical noise signals to target neural tissue, non-neural tissue, or a combination thereof via the electrode, and the controller is configured to tune the broad spectrum of electrical noise signals to optimize the therapy provided to the patient based on feedback received from the patient.

For example, the method and system can include applying a broad spectrum of tunable electrical noise signals to target neural tissue, non-neural tissue, or a combination thereof located within or adjacent the patient's brain or spinal cord, a dorsal root ganglion, a sympathetic chain ganglion, a cranial nerve, an autonomic nerve (e.g., parasympathetic and/or sympathetic nerves), or a peripheral nerve, as described in more detail below, where the delivery of the broad spectrum of tunable electrical noise signals can be tuned or adjusted based on patient feedback to treat a specific condition, illness, disease state, symptom, etc.

Specifically, the therapy provided to the patient through the broad spectrum of tunable electrical noise signals can treat pain (e.g., chronic pain), an autonomic disorder (e.g., diabetic peripheral neuropathy, hypertension, hypotension, complex regional pain syndrome (CRPS), Raynaud's syndrome, overactive bladder, urinary incontinence, fecal incontinence, fecal constipation, migraine, etc.), a sensory disorder (e.g., tinnitus, hearing loss, vertigo, etc.), a motor disorder (e.g., Huntington's disease, Parkinson's disease, Multiple Sclerosis, spinal muscular atrophy (SMA), dystonia, essential tremor, etc.), or a combination thereof. Further, the therapy provided to the patient can elicit plastic changes in neural tissue, non-neural tissue, or a combination thereof to mitigate or abolish a pathophysiologic disease or syndrome. Plastic changes are changes to the neural tissue, non-neural tissue, or a combination thereof in response to physiological demands. Such plastic changes can include morphological and functional changes.

In some embodiments, the broad spectrum of electrical noise signals can be tuned based on patient feedback by adjusting energy contained within a frequency band, while in other embodiments, the broad spectrum of electrical noise signals can be tuned based on patient feedback by adjusting a phase component of the electrical signal. For example, one or more electrodes can be implanted, inserted percutaneously, or positioned transcutaneously such that the electrodes are nearby the target neural tissue, non-neural tissue and combination thereof as necessary to treat their disease or syndrome. A noise generator can then be instructed to deliver a broad spectrum of electrical noise signals through the one or more electrodes. The patient and/or caregiver can then "program" the optimal stimulation waveform by operating a controller. The controller can tune the waveform associated with the broad spectrum of electrical noise signal being delivered to the patient by adjusting energy levels within a particular frequency band, and for all frequency bands delivered, to best treat the patient.

Figure 11A:
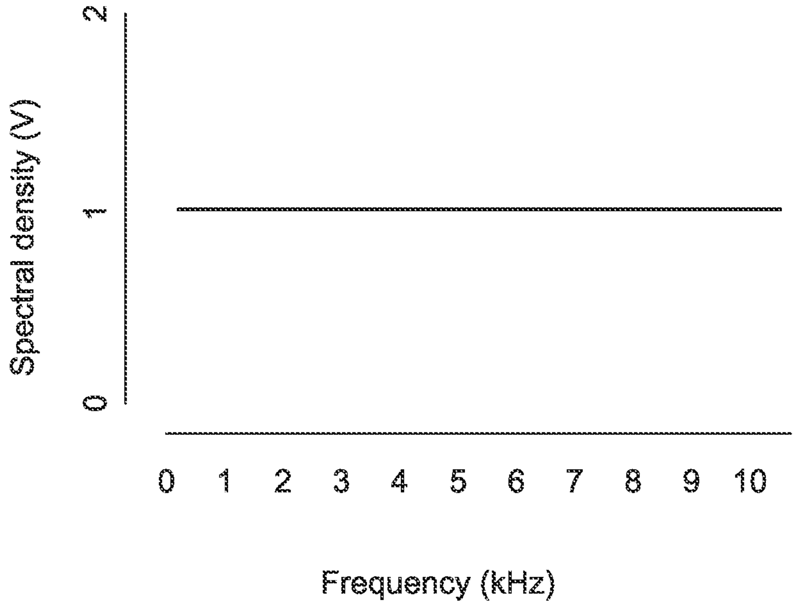
FIG. 11A is a simplified graph of an original power spectrum for a broad spectrum of electrical noise signals.
Figure 11B:
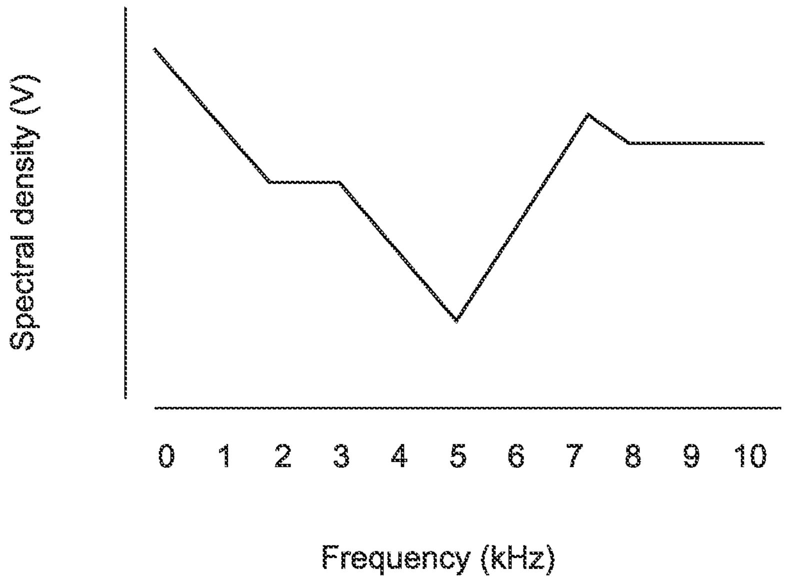
FIG. 11B is a simplified graph of a power spectrum for a broad spectrum of electrical noise signals that has been tuned based on patient feedback.

For example, the controller can tune the waveform associated with the broad spectrum of electrical noise signals by dividing its frequency range into a series of frequency bands, and amplifying or attenuating the power within an individual frequency band or combinations of frequency bands until patient feedback indicates an optimal therapeutic benefit. In another example, the controller can tune the electrical noise signals by amplifying, attenuating, and/or shifting the phase components of the electrical noise signal until the feedback received from the patient indicates an optimal therapeutic benefit. The controller can tune the electrical noise signals while the patient is stationary or active, and with feedback from the user. In another embodiment, multiple noise generators (or multiple noise signal generators) may be driven by the controller to simultaneously power individual frequency bands as described herein. By way of example, FIG. 11A shows the spectral density of a broad spectrum of electrical noise signals, and FIG. 11B shows the broad spectrum of electrical noise signals after it has been tuned to best treat the particular patient based on feedback received from the patient in a manner consistent with the technologies described herein. It should be appreciated that FIG. 11B depicts a simplified version of an actual tuned electrical noise signal for explanatory purposes.

The tunability feature contemplated by the technologies described herein allows for the therapy provided to the patient to be tuned, altered, adjusted, etc. based on feedback received from the patient, the specific symptoms or disease state being treated, the physical characteristics of the patient, the mental characteristics of the patient, and/or the current activity level of the patient, where each of these variables can affect how the originally applied broad spectrum of electrical noise signals provides therapeutic benefit to the patient. Feedback can be provided by the patient based on self-report (e.g., introspection, observations of unwanted sensory- and/or motor activity, autonomic dysfunction, etc.), determined from data generated by sensors measuring physiological outcomes, based on data from artificial intelligence or machine learning systems (e.g., output or feedback data), or based on combinations thereof.

In some embodiments, the broad spectrum of electrical noise signals can be tuned based on patient feedback describing unwanted sensations. Examples of unwanted sensations include pain and other sensations, such as urinary urgency and fecal urgency. Other examples include unwanted sensations of touch, vibration, pressure, tightness, feelings of warmth or cold, numbness, sounds of ringing (or buzzing, hissing, clicking, roaring, humming), anxiety, dizziness, aura, loss of sound intensity, and/or loss of sound quality. Any of the unwanted sensations described above can occur in the absence of an external stimulus and/or when the patient is perfectly still.

In some embodiments, the broad spectrum of electrical noise signals can be tuned based on patient feedback describing physiological outcomes. It should be appreciated that the physiological outcomes may be reported by the patient, observed by a clinician, evaluated based on data generated by one or more sensors, and/or otherwise determined depending on the particular embodiment. Examples of physiological outcomes that can be used to tune the broad spectrum of electrical noise signals include those pertaining to bladder and bowel function, such as incontinence, constipation, voided volumes, voiding pressures, voiding frequency, and electromyogram signals of the urinary and colonic ensemble. Other examples of physiological outcomes that can be used to tune the broad spectrum of electrical noise signals include those pertaining to motor function, such as electromyogram signals, strength, weakness, stiffness, spasm, contracture, tremors, spasticity, atrophy, bradykinesia, and paralysis. Other markers of physiological activity that could be used to tune the broad spectrum of noise signals include electroencephalogram signals, evoked brain potentials, and cognitive changes including dementia, hallucination, and delusion. Markers of autonomic function can also be used to tune the broad spectrum of electrical noise signals, such as heart-rate, blood flow, blood pressure, respiration, nausea, sweat production, skin color, and edema. Any of the physiological changes described above can be used to tune the broad spectrum of noise signals in the absence of an external stimulus or when the patient is perfectly still. In some embodiments, sensor types include biopotential electrodes, pressure sensors and flow meters, chemical sensors, and/or temperature sensors. It should be appreciated that, in some embodiments, one or more of the sensors can act in a close-loop fashion to tune the broad spectrum of electrical noise signals to provide and optimize therapy.

Whether the broad spectrum of tunable electrical noise signals is being applied to target neural tissue, non-neural tissue, or a combination thereof located within or adjacent the patient's brain or spinal cord, a dorsal root ganglion, a sympathetic chain ganglion, a cranial nerve, autonomic circuitry, or a peripheral nerve, the technologies described herein illustrate that the specific parameters of the broad spectrum of tunable electrical noise signals and the location of the electrodes through which the broad spectrum of tunable electrical noise signals is delivered can be selectively controlled to provide improved symptom relief and therapy to the patient for the treatment of pain, autonomic disorders, sensory disorders, motor disorders, etc. The specific system and parameters are discussed in more detail below.

Referring now to FIG. 1, there is illustrated a system 50 for delivering a broad spectrum of tunable electrical noise signals to provide therapy to a patient 116, where the target neural tissue, non-neural tissue, or a combination thereof 135 is located within or adjacent tissue within the patient's brain 134. In general, the system 50 in FIG. 1 can include one or more electrodes 107 (shown diagrammatically in FIG. 1 and not in any specific detail) that are connected by an electrical lead 108 to a noise generator 109. In various embodiments, one or more electrodes 107 (or electrical contacts) may be embodied on, form a portion of, or be electrically coupled to one or more electrical leads 108 that are electrically (or electromagnetically) coupled to the noise generator 109. An additional lead 117 can be used to couple the noise generator 109 to the rest of the system 50, which can include a user interface 112 and a controller 110, where it is to be understood that as an alternative to the use of the lead 117, the noise generator 109 can be wirelessly connected to the rest of the system 50. The system can also include a power system 111 and/or a patient monitor system. Further, it should be understood that while the system 50 of FIG. 1 illustrates a configuration where a broad spectrum of tunable electrical noise signals can be delivered to target neural tissue, non-neural tissue, or a combination 135 thereof utilizing an electrode 107 coupled to an implantable noise generator 109 via a lead 108, the electrode 107 can alternatively be coupled to an external noise generator via a wireless antenna system. In addition, in some embodiments, more than one electrode 107 can be used. Regardless of the exact type (e.g., percutaneous, transcutaneous, implantable, etc.) or configuration (e.g., monopolar, bipolar, multipolar, etc.) of the electrode(s) 107, the electrode(s) 107 can be in the form of an electrode assembly that can deliver a broad spectrum of tunable electrical noise signals to a patient to provide therapy to the patient and/or improve one or more of the patient's symptoms. Specific diseases or conditions that can be treated based on stimulation of the brain include, for example, Parkinson's disease, essential tremor, depression, obsessive compulsive disorder, Tourette's syndrome, epilepsy, schizophrenia, narcolepsy, seizures, Alzheimer's disease, tinnitus, Meniere's disease, and chronic pain.

Figure 2:
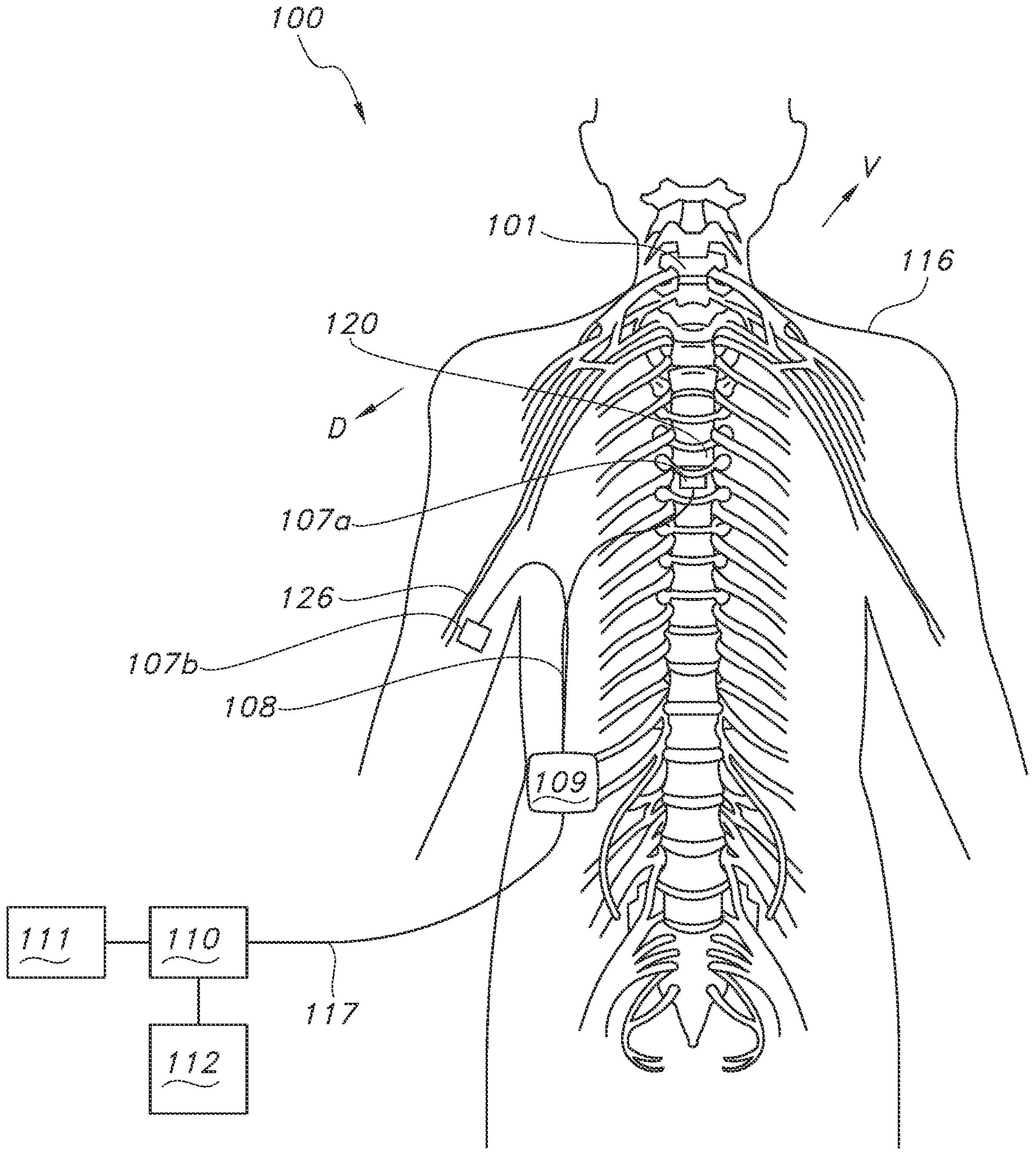
FIG. 2 illustrates at least one embodiment of a system for delivering a broad spectrum of electrical noise signals to target neural tissue, non-neural tissue, or a combination thereof in a patient, where the electrical noise signals are tunable, and where the target tissue is located within or adjacent the spinal cord.

Referring now to FIG. 2, there is illustrated a system 100 for delivering a broad spectrum of tunable electrical noise signals to provide therapy to a patient, where the target neural tissue, non-neural tissue, or a combination thereof is located within or adjacent the spinal cord 101 of a patient 116. As shown in FIG. 2, the system 100 can include multiple devices to control and deliver a broad spectrum of tunable electrical noise signals to one or more areas of target neural tissue, non-neural tissue, or a combination thereof located within or adjacent the spinal cord 101 to provide therapy to a patient 116. In general, the system 100 in FIG. 2 can include one or more electrodes **107*a* and/or 107*b* (shown diagrammatically in FIG. 2 and not in any specific detail) that are connected by one or more electrical leads 108 to a noise generator 109. An additional lead 117 can be used to couple the noise generator 109 to the rest of the system 100, which can include a user interface 112 and a controller 110, where it is to be understood that as an alternative to the use of the lead 117, the noise generator 109 can be wirelessly connected to the rest of the system 50. The system can also include an isolated power system 111 and/or a patient monitor system. Further, it should be understood that while the system 100 of FIG. 2 illustrates a configuration where a broad spectrum of tunable electrical noise signals can be delivered to target neural tissue, non-neural tissue, or a combination thereof utilizing electrodes 107*a* and/or 107*b* coupled to an implantable noise generator 109 via a lead 108, the electrodes 107*a* and/or 107*b* can alternatively be coupled to an external noise generator via a wireless antenna system. Regardless, the electrodes 107*a* and/or 107*b* can be in the form of an electrode assembly that can deliver a broad spectrum of tunable electrical noise signals to a patient to provide therapy to the patient and/or improve one or more of the patient's symptoms based on the specific location of the electrodes, as discussed in more detail in FIGS. 3-7** below.

Figure 3:
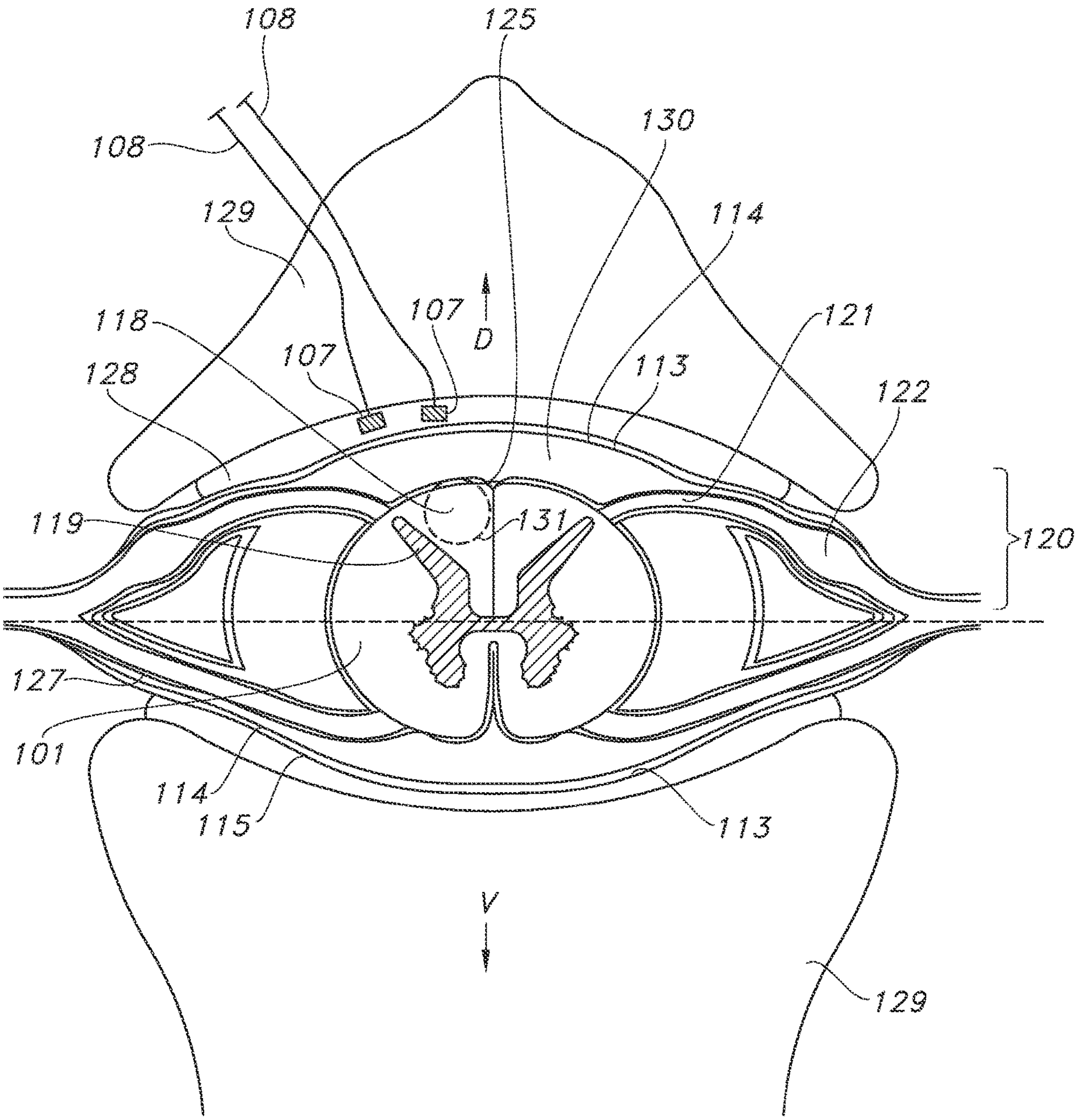
FIG. 3 is a zoomed-in view of the spinal cord and illustrates at least one option for electrode placement according to the system of FIG. 2, where the target tissue is located within or adjacent a dorsal region of the spinal cord, such as the dorsal columns.

Referring now to FIG. 3, the placement of the electrode or electrodes 107 in order to deliver a broad spectrum of tunable electrical noise signals to an area within or adjacent target neural tissue, non-neural tissue, or a combination thereof 131 located adjacent a dorsal region 120 of the spinal cord 101, and in particular a dorsal column 118, is discussed in more detail, where the dorsal D and ventral V directions of the spinal cord 101 are labeled for reference purposes. For instance, one or more electrodes 107 can be positioned within a portion of the epidural space 128 of the patient 116 adjacent a dorsal region 120 of the spinal cord 101, where the dorsal region 120 of the spinal cord 101 can be identified via locating the posterior median sulcus 125. As shown, the epidural space 128 is positioned between the bone 129 (vertebrae) and the dura mater 115. Thus, a broad spectrum of tunable electrical noise signals transmitted by the electrode 107 must be configured to pass through the dura mater 115, subdural cavity 113, arachnoid mater 114, subarachnoid cavity 130, and pia mater 127 to reach the target neural tissue, non-neural tissue, or a combination thereof 131 and deliver the desired broad spectrum of tunable electrical noise signals therein. By placing the electrode or electrodes 107 in the epidural space 128 adjacent a dorsal region 120 of the spinal cord 101, a broad spectrum of tunable electrical noise signals can be delivered to target neural tissue, non-neural tissue, or a combination thereof 131 located within or adjacent a dorsal column 118 to provide therapy to the patient. It is also to be understood that the electrode or electrodes 107 can be positioned in any suitable location in the dorsal region 120 of the spinal cord 101 in order to deliver a broad spectrum of tunable electrical noise signals to an area within or adjacent other target neural tissue, non-neural tissue, or a combination thereof, such as tissue located adjacent a dorsal horn 119 or a dorsal root 121. Specific diseases or conditions that can be treated based on stimulation of the dorsal region of the spinal cord, and in particular, the dorsal columns include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, cervical neuritis, post herpetic neuralgia, vertigo, tinnitus, hearing loss and inflammatory pain such as arthritis, irritable bowel pain, osteoarthritis pain, and fibromyalgia.

Figure 4:
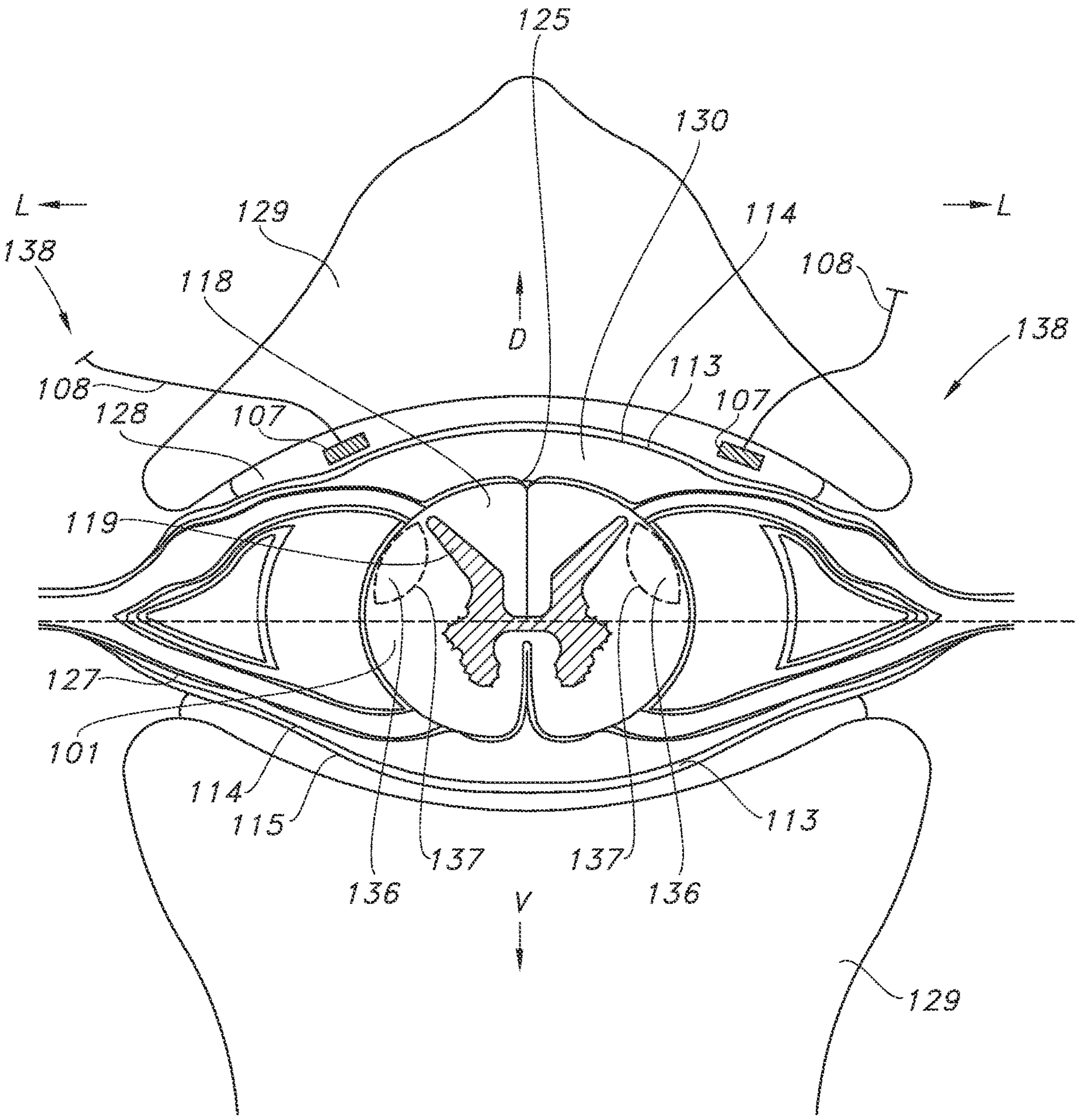
FIG. 4 is a zoomed-in view of the spinal cord and illustrates at least one other option for electrode placement according to the system of FIG. 2, where the target tissue is located within or adjacent to the dorsolateral region of the spinal cord, such as the dorsolateral funiculus.

Referring now to FIG. 4, the placement of the electrode or electrodes 107 in order to deliver a broad spectrum of tunable electrical noise signals to an area within or adjacent target neural tissue, non-neural tissue, or a combination thereof 137 located in a dorsolateral region 138 of the spinal cord 101 is discussed in more detail, where the dorsal D, ventral V, and lateral L directions are labeled for reference purposes. For instance, one or more electrodes 107 can be positioned adjacent a dorsolateral region 138 of the spinal cord 101. By placing the electrode or electrodes 107 adjacent a dorsolateral region 138 of the spinal cord 101, a broad spectrum of tunable electrical noise signals can be delivered to target neural tissue, non-neural tissue, or a combination thereof 137 located within or adjacent a dorsolateral region 138 of the spinal cord 101 to provide therapy to the patient. Specifically, nerve fiber activity in the right or left dorsolateral funiculus 136 or a combination thereof can be altered via a broad spectrum of tunable electrical noise signals in order to treat or alleviate symptoms associated various conditions. Specific diseases or conditions that can be treated based on stimulation of the dorsolateral region of the spinal cord, and in particular, the dorsolateral funiculus include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, cervical neuritis, post herpetic neuralgia, vertigo, tinnitus, hearing loss and inflammatory pain such as arthritis, irritable bowel pain, osteoarthritis pain, and fibromyalgia.

Figure 5:
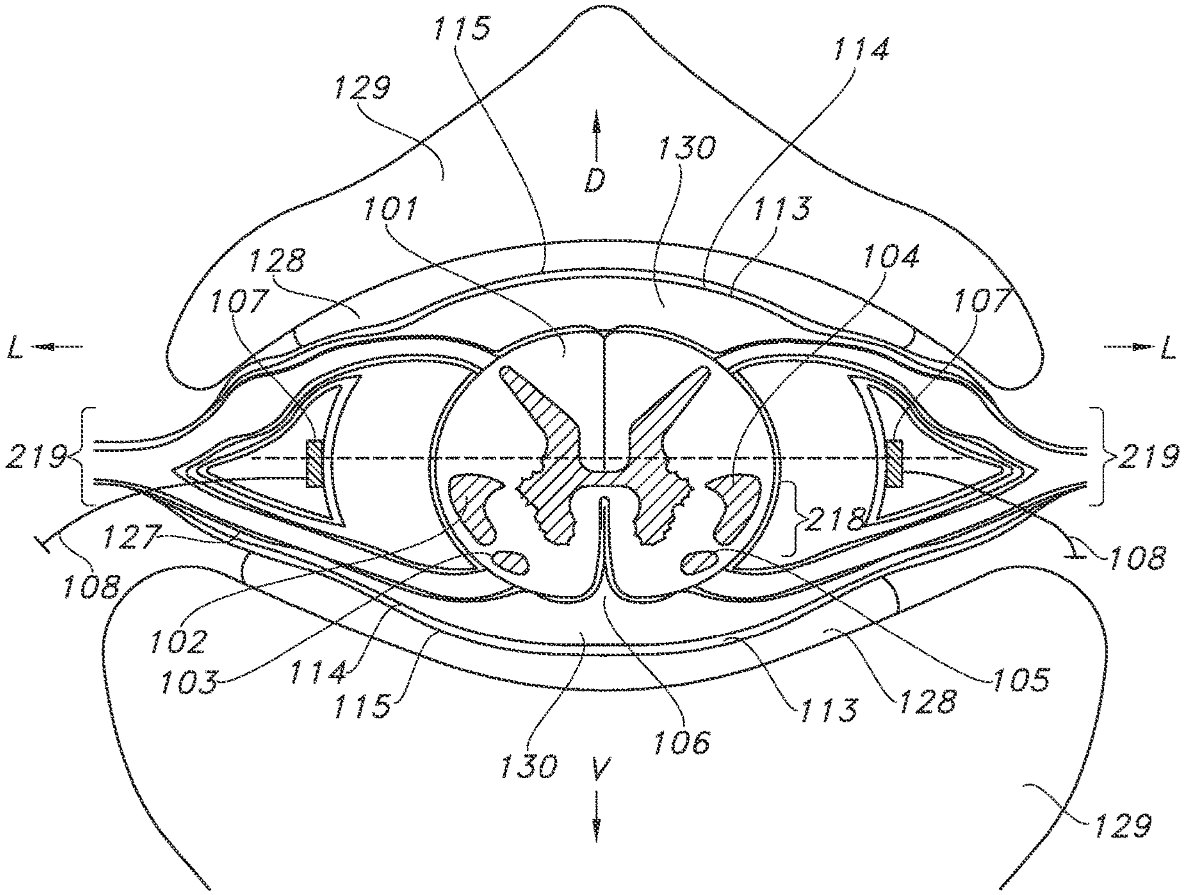
FIG. 5 is a zoomed-in view of the spinal cord and illustrates at least one other option for electrode placement according to the system of FIG. 2, where the target tissue is located within or adjacent the lateral region of the spinal cord, such as the spinothalamic tract.

Referring now to FIG. 5, the placement of the electrode or electrodes 107 in order to deliver a broad spectrum of tunable electrical noise signals to an area within or adjacent target neural tissue, non-neural tissue, or a combination thereof 218 located in a lateral region 219 of the spinal cord 101 is discussed in more detail, where the dorsal D, ventral V, and lateral L directions are labeled for reference purposes. For instance, one or more electrodes 107 can be positioned adjacent a lateral region 219 of the spinal cord 101. By placing the electrode or electrodes 107 adjacent lateral region 219 of the spinal cord 101, a broad spectrum of tunable electrical noise signals can be delivered to target neural tissue, non-neural tissue, or a combination thereof 218 located within or adjacent a lateral region 219 of the spinal cord 101 to provide therapy to the patient. Specifically, nerve fiber activity in the right lateral spinothalamic tract 102, the left lateral spinothalamic tract 104, or a combination thereof can be altered via a broad spectrum of tunable electrical noise signals in order to treat or alleviate symptoms associated various conditions. Moreover, it is to be understood that nerve fiber activity in the right anterior spinothalamic tract 103, the left anterior spinothalamic tract 105, or a combination thereof can also be altered via a broad spectrum of tunable electrical noise signals based on the specific positioning of the one or more electrodes 107. Specific diseases or conditions that can be treated based on stimulation of the lateral region of the spinal cord, and in particular, the lateral spinothalamic tract include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, cervical neuritis, post herpetic neuralgia, vertigo, tinnitus, hearing loss and inflammatory pain such as arthritis, irritable bowel pain, osteoarthritis pain, and fibromyalgia.

Figure 6:
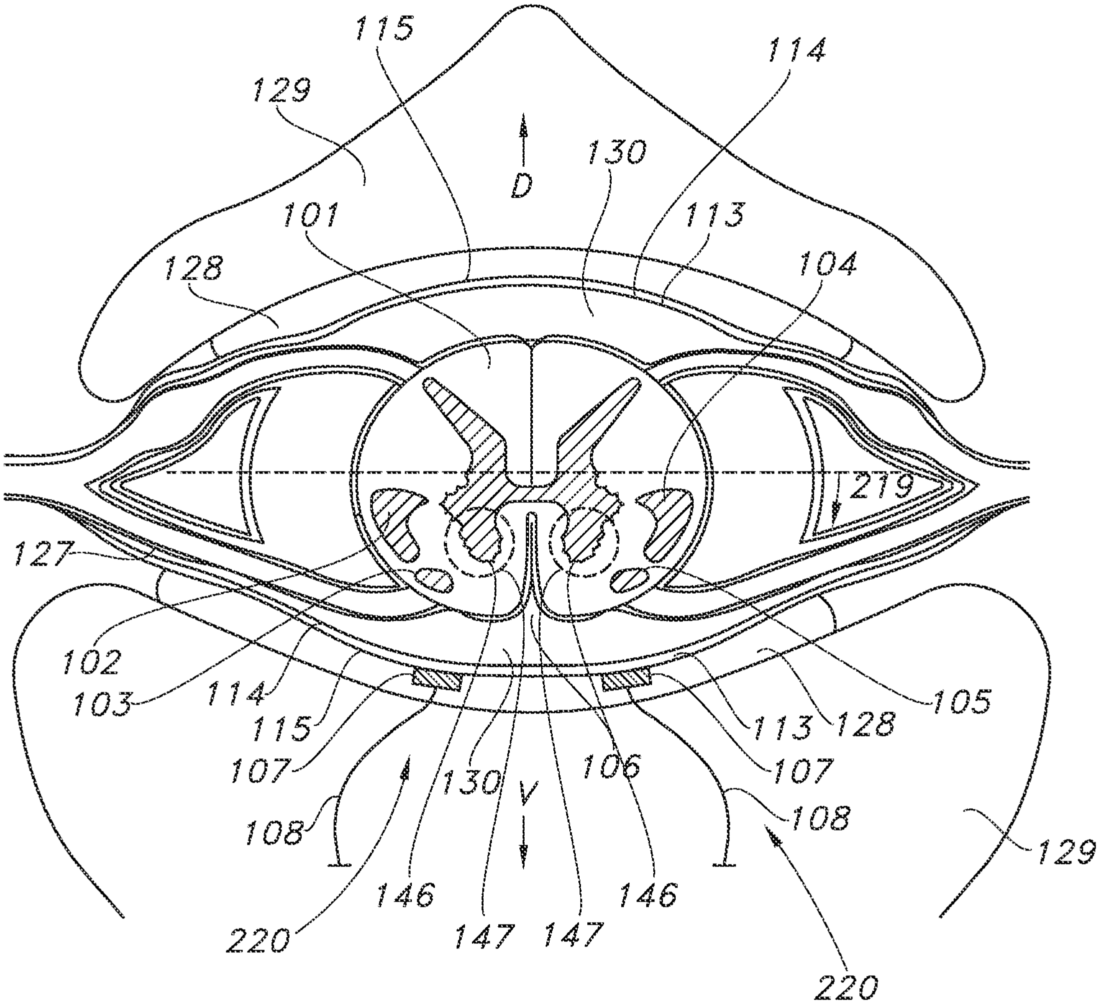
FIG. 6 is a zoomed-in view of the spinal cord and illustrates at least one other option for electrode placement according to the system of FIG. 2, where the target tissue is located with or adjacent the ventral region of the spinal cord, such as the ventral horn.

Referring now to FIG. 6, the placement of the electrode or electrodes 107 in order to deliver a broad spectrum of tunable electrical noise signals to an area within or adjacent target neural tissue, non-neural tissue, or a combination thereof 147 located in a ventral region 220 of the spinal cord 101 is discussed in more detail, where the dorsal D and ventral V directions are labeled for reference purposes. For instance, one or more electrodes 107 can be positioned within a portion of the epidural space 128 of the patient 116 adjacent a ventral region 220 of the spinal cord 101, where the ventral region 220 of the spinal cord 101 can be identified via locating the anterior median fissure 106. As shown, the epidural space 128 is positioned between the bone 129 (vertebrae) and the dura mater 115. Thus, a broad spectrum of tunable electrical noise signals transmitted by the electrode 107 must be configured to pass through the dura mater 115, subdural cavity 113, arachnoid mater 114, subarachnoid cavity 130, and pia mater 127 to reach the target neural tissue, non-neural tissue, or a combination thereof 147 and deliver the desired broad spectrum of tunable electrical noise signals therein. By placing the electrode or electrodes 107 in the epidural space 128 adjacent a ventral region 220 of the spinal cord 101, a broad spectrum of tunable electrical noise signals can be delivered to target neural tissue, non-neural tissue, or a combination thereof 147 located in a ventral region 220 of the spinal cord 101 to provide therapy to the patient. Specifically, in one particular embodiment, nerve fiber activity in the right or left ventral horn 146 or a combination thereof can be altered via a broad spectrum of tunable electrical noise signals in order to treat or alleviate symptoms associated various conditions. Specific diseases or conditions that can be treated based on stimulation of the ventral region of the spinal cord include, for example, motoneuron disease (amyotrophic lateral sclerosis; progressive muscular atrophy; progressive bulbar palsy; primary lateral sclerosis; hereditary spastic paraplegia), spinal muscular atrophy (infantile and juvenile spinal muscular atrophy; focal amyotrophy), and multiple sclerosis.

Figure 7:
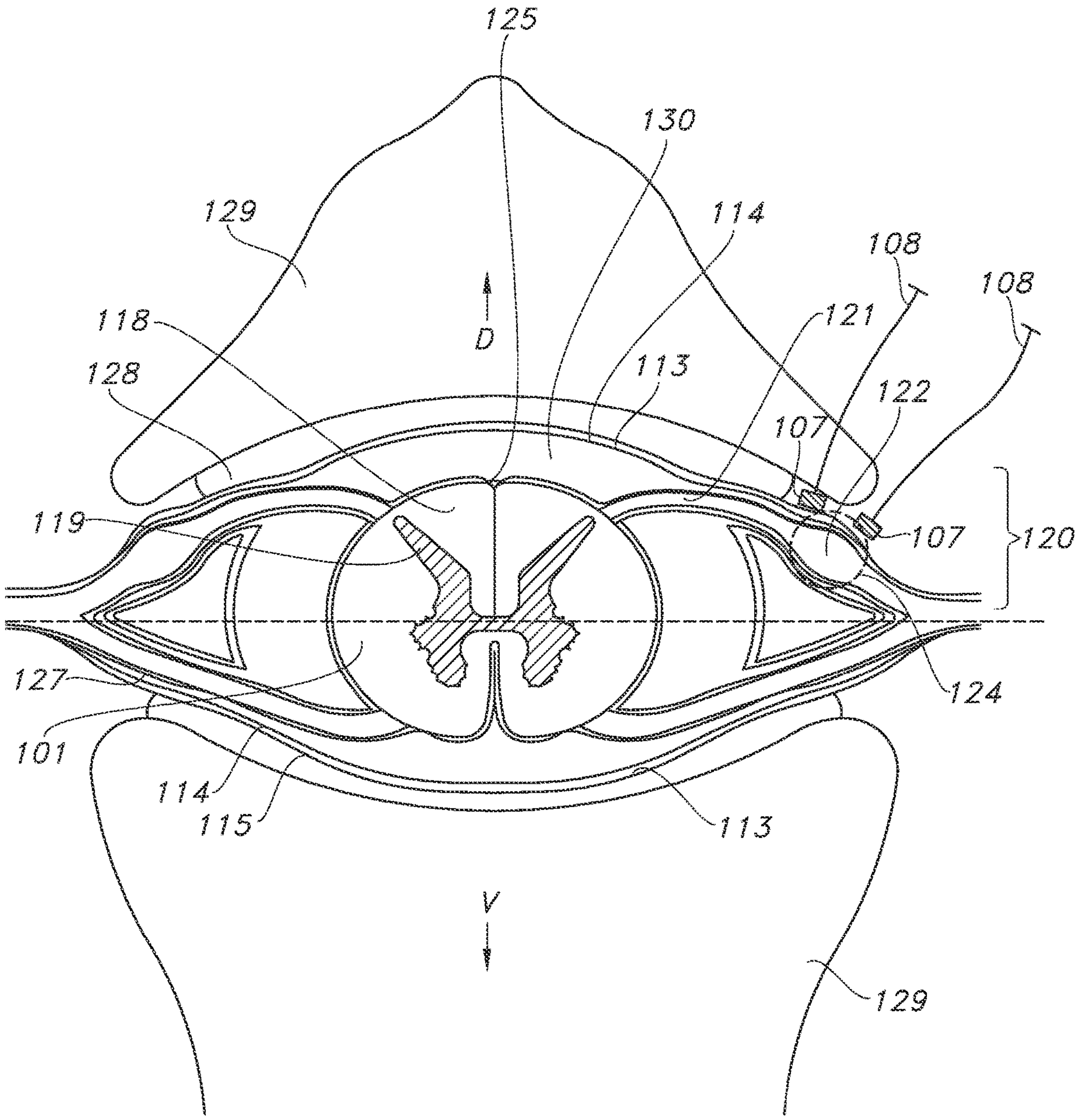
FIG. 7 is a zoomed-in view of the spinal cord and illustrates at least one other option for electrode placement according to the system of FIG. 2, where the target tissue is located within or adjacent a dorsal root ganglion.

Referring now to FIG. 7, the placement of the electrode or electrodes 107 in order to deliver a broad spectrum of tunable electrical noise signals to an area within or adjacent target neural tissue, non-neural tissue, or a combination thereof 124 located adjacent or near a dorsal region 120 of the spinal cord 101, and in particular a dorsal root ganglion 122, is discussed in more detail, where the dorsal D and ventral V directions of the spinal cord 101 are labeled for reference purposes. For instance, one or more electrodes 107 can be positioned within a portion of the epidural space 128 of the patient 116 adjacent a dorsal (or posterior) portion 120 of the spinal cord 101, where the dorsal (or posterior) portion 120 of the spinal cord 101 can be identified via locating the posterior median sulcus 125. As shown, the epidural space 128 is positioned between the bone 129 (vertebrae) and the dura mater 115. Thus, a broad spectrum of tunable electrical noise signals transmitted by the electrode 107 must be configured to pass through the dura mater 115, subdural cavity 113, arachnoid mater 114, subarachnoid cavity 130, and pia mater 127 to reach the target neural tissue, non-neural tissue, or a combination thereof 124 and deliver the desired broad spectrum of tunable electrical noise signals therein. By placing the electrode or electrodes 107 in the epidural space 128 adjacent a dorsal D (or posterior) portion 120 of the spinal cord 101, a broad spectrum of tunable electrical noise signals can be delivered to target neural tissue, non-neural tissue, or a combination thereof 124 located within or adjacent a dorsal root ganglion 122 to provide therapy to the patient. Specific diseases or conditions that can be treated based on stimulation of the dorsal root ganglion include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, cervical neuritis, post herpetic neuralgia, vertigo, tinnitus, hearing loss and inflammatory pain such as arthritis, irritable bowel pain, osteoarthritis pain and fibromyalgia.

Figure 8:
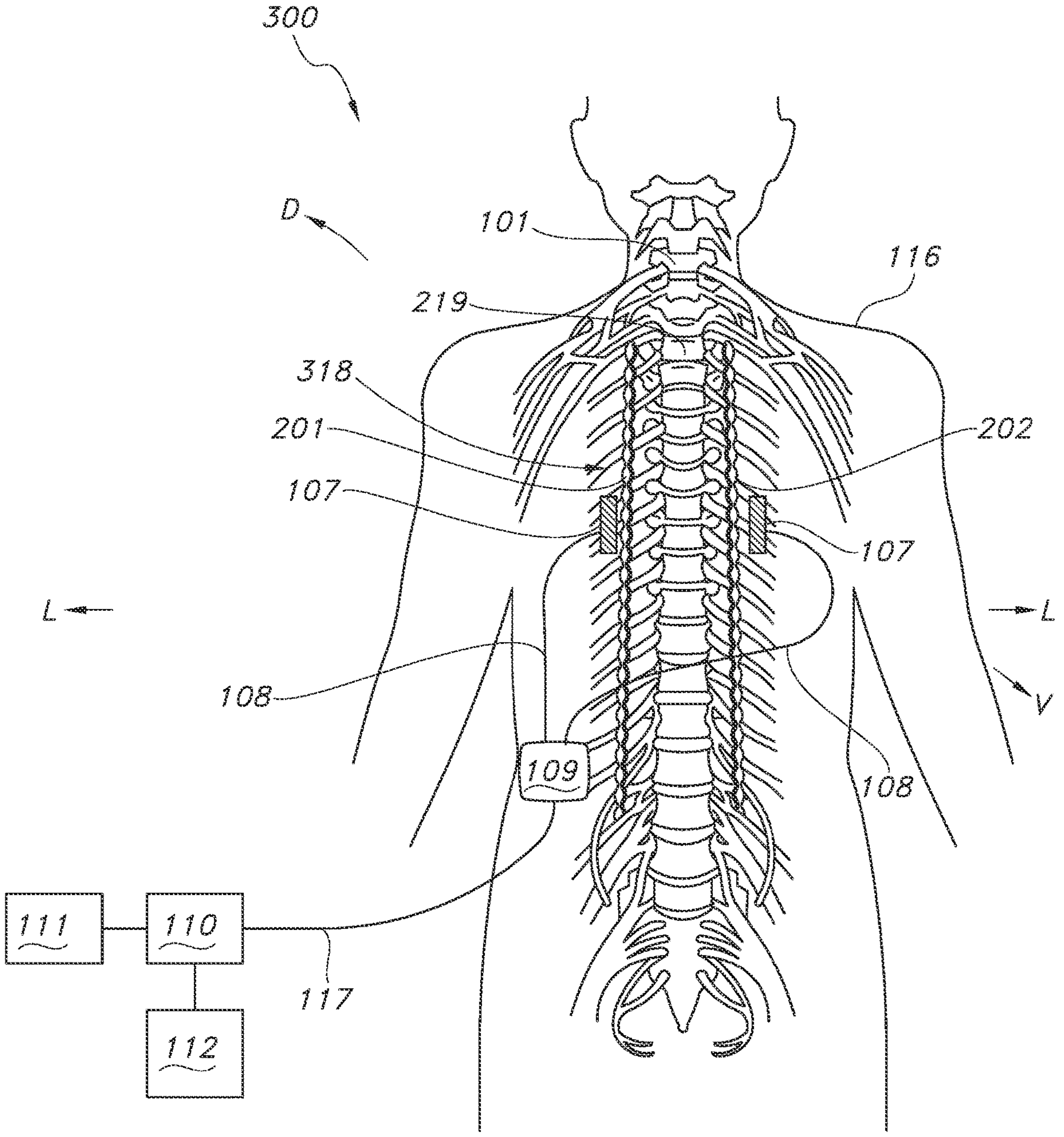
FIG. 8 illustrates at least one embodiment of a system for delivering a broad spectrum of electrical noise signals to target neural tissue, non-neural tissue, or a combination thereof in a patient, where the electrical noise signals are tunable, and where the target tissue is located within or adjacent a sympathetic chain ganglion.
Figure 9:
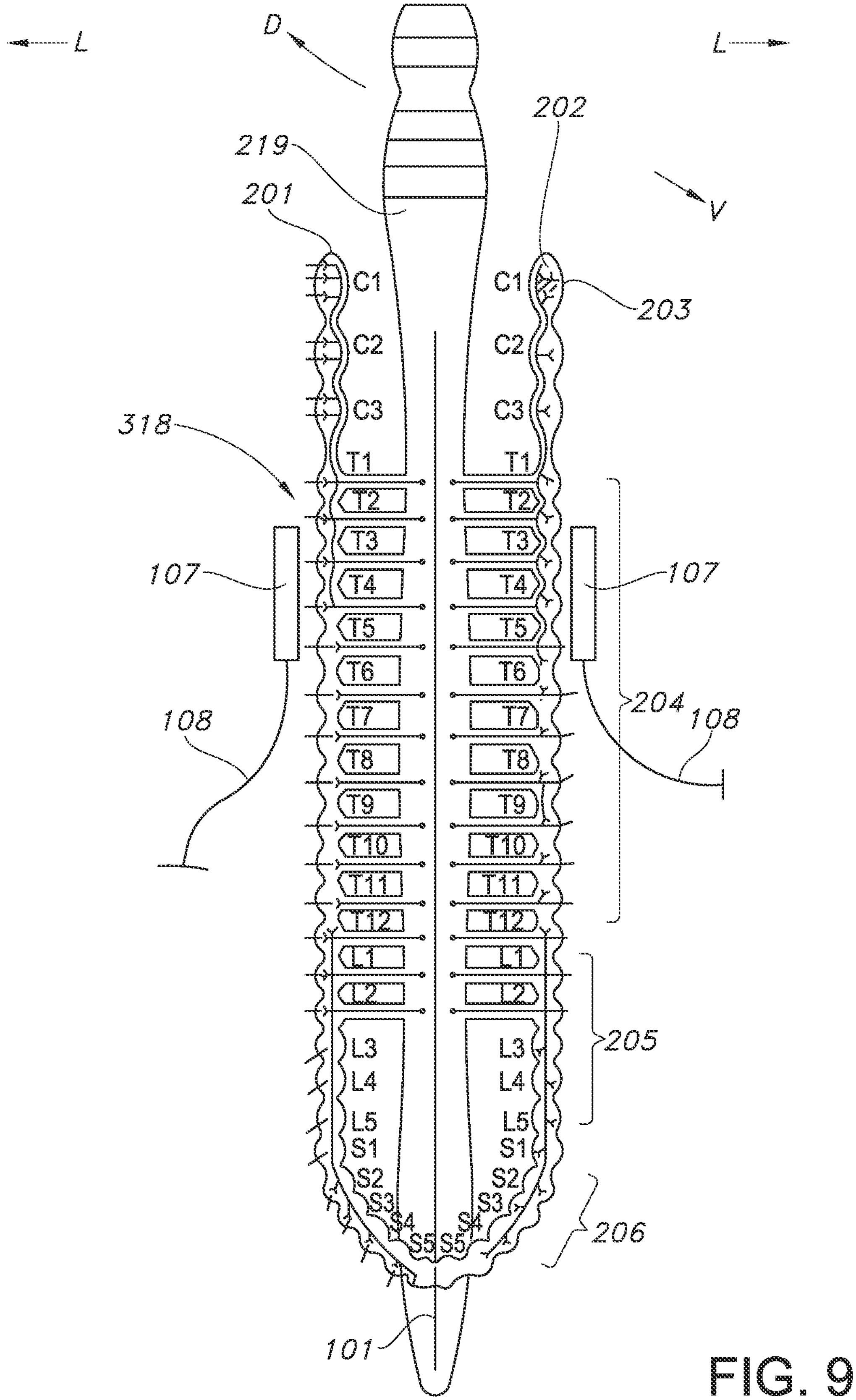
FIG. 9 is a zoomed-in view of the sympathetic chain and illustrates at least one option for electrode placement according to the system of FIG. 8.

Referring now to FIG. 8, there is illustrated a system 300 for delivering a broad spectrum of tunable electrical noise signals to provide therapy to a patient 116, where the target neural tissue, non-neural tissue, or a combination thereof 318 located adjacent a ventral or anterior region 219 of a spinal cord 101 of the patient 116. It should be appreciated that the system 300 of FIG. 8 may include similar elements and/or features to the system 50 described in reference to FIG. 1. In particular, the target neural tissue, non-neural tissue, or a combination thereof 318 can be a sympathetic chain ganglion located in the right sympathetic chain 201, the left sympathetic chain 202, or a combination thereof. As shown in FIG. 9, in some embodiments, the system 300 can include multiple devices to control and deliver a broad spectrum of tunable electrical noise signals to an area within or adjacent target neural tissue, non-neural tissue, or a combination thereof 318 located adjacent a ventral V (or anterior) region 219 of the spinal cord 101 to provide therapy to the patient 116. In general, the system 300 of FIG. 8 can include one or more electrodes 107 (shown diagrammatically in FIG. 8 and not in any specific detail) that are connected by an electrical lead 108 to a noise generator 109. An additional lead 117 can be used to couple the noise generator 109 to the rest of the system 300, which can include a user interface 112, and a controller 110, where it is to be understood that as an alternative to the use of the lead 117, the noise generator 109 can be wirelessly connected to the rest of the system 50. The system may also include an isolated power system 111 and/or a patient monitor system. Further, it should be understood that while the system 300 of FIG. 8 illustrates a configuration where a broad spectrum of tunable electrical noise signals can be delivered to target neural tissue, non-neural tissue, or a combination thereof utilizing an electrode or electrodes 107 coupled to an implantable noise generator 109 via a lead 108, the electrode or electrodes 107 can alternatively be coupled to an external noise generator via a wireless antenna system. Regardless, the electrode or electrodes 107 can be in the form of an electrode assembly that can that can deliver a broad spectrum of tunable electrical noise signals to a patient to provide therapy to the patient and/or improve one or more of the patient's symptoms.

Referring now to FIG. 9, the placement of the electrode or electrodes 107 is discussed in more detail. For instance, one or more electrodes 107 can be positioned adjacent a region of the right sympathetic chain 201 or the left sympathetic chain 202 of the patient 116, where the sympathetic chains 201 and 202 are located ventral and lateral to a ventral (or anterior) region 219 of the spinal cord 101. By placing the electrode or electrodes 107 adjacent target neural tissue, non-neural tissue, or a combination thereof 318 located lateral and ventral to a ventral (or anterior) region 219 of the spinal cord 101, a broad spectrum of tunable electrical noise signals can be delivered to the target neural tissue, non-neural tissue, or a combination thereof 318 (e.g., a ganglion or ganglia of the right sympathetic chain 201 or the left sympathetic chain 202) to provide therapy to the patient.

For instance, a broad spectrum of tunable electrical noise signals can be delivered to a ganglion or ganglia associated with the cervical portion 203, the thoracic portion 204, the lumbar portion 205, or the sacral portion 206 of the right sympathetic chain 201 or the left sympathetic chain 202, or any combination thereof to provide therapy to the targeted area or areas. In one particular embodiment, an electrode 107 can be placed adjacent the cervical region 203 of the sympathetic chain to affect nerve fiber activity associated with levels C1-C3, which can affect nerve fiber activity associated with the eyes, the lachrymal glands, the salivary glands, and the sweat glands, hair follicles, and blood vessels of the head, neck, and arms. In another embodiment, an electrode 107 can be placed adjacent levels T1-T4 of the thoracic region 204, which can affect nerve fiber activity associated with the heart and lungs. In an additional embodiment, an electrode 107 can be placed adjacent levels T5-T9 of the thoracic region 204, which can affect nerve fiber activity associated with the stomach, duodenum, pancreas, liver, kidneys, and adrenal medulla. In yet another embodiment, an electrode 107 can be placed adjacent levels T10-T11 of the thoracic region 204, which can affect nerve fiber activity associated with the stomach and duodenum. In one more embodiment, an electrode 107 can be placed adjacent level T12 of the thoracic region 204 and levels L1-L3 of the lumbar region 205, which can affect nerve fiber activity in the colon, rectum, bladder, and external genitalia. In still another embodiment, an electrode 107 can be placed adjacent levels L4-L5 of the lumbar region 205 and levels S1-S3 of the sacral region 206, which can affect nerve fiber activity associated with the sweat glands, hair follicles, and blood vessels of the lower limbs. In another embodiment, an electrode 107 can be placed adjacent levels S4-S5 of the sacral region 206, which can affect nerve fiber activity associated with the sweat glands, hair follicles, and blood vessels of the perineum. Specific diseases or conditions that can be treated based on stimulation of a sympathetic nervous system include, for example, complex regional pain syndrome, peripheral vascular disease and chronic limb ischemia, angina pain, diabetic pain, abdominal/visceral pain syndrome, phantom limb pain, Raynaud's syndrome, diabetic peripheral neuropathy, hypertension, hypotension, headache and migraine, and inflammatory pain such as arthritis, irritable bowel pain, osteoarthritis pain, and fibromyalgia. It should be appreciated that, in some embodiments, the electrode(s) 107 may be placed beside other autonomic structures including parasympathetic nerves (e.g., vagus nerve).

Figure 10:
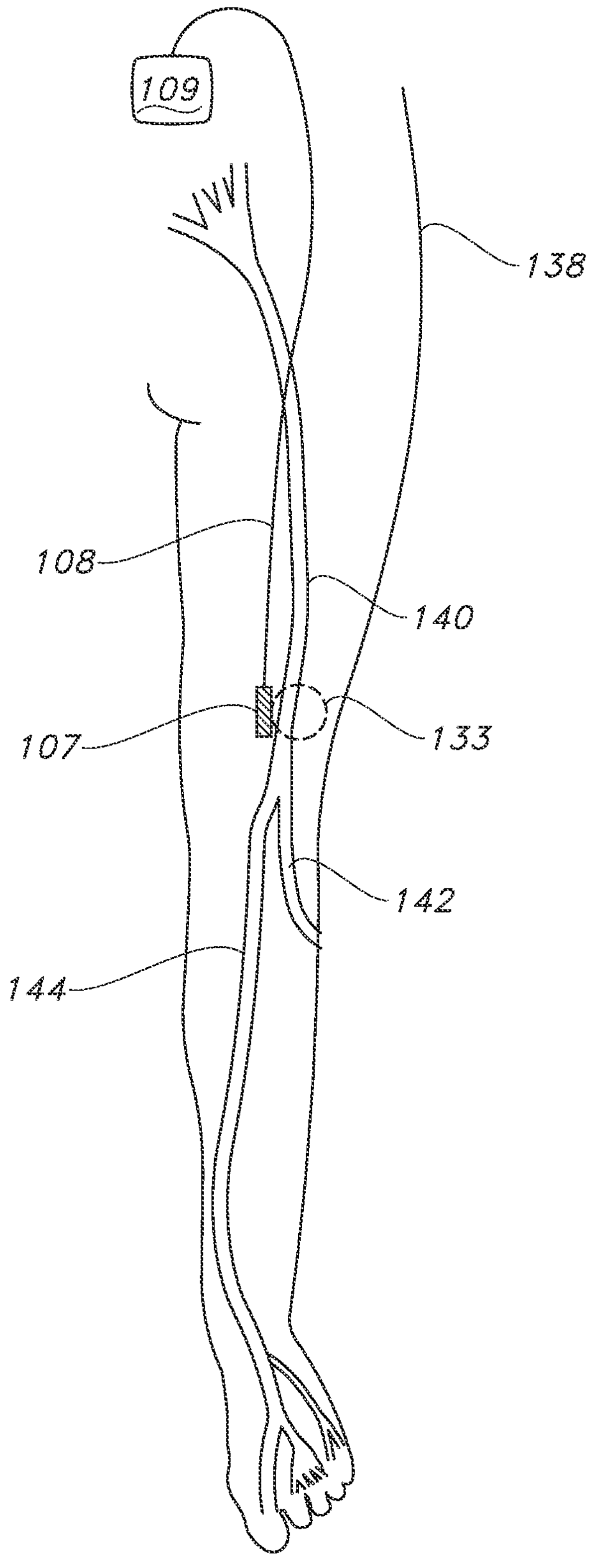
FIG. 10 illustrates at least one embodiment of a system for delivering a broad spectrum of electrical noise signals to target neural tissue, non-neural tissue, or a combination thereof in a patient, where the electrical noise signals are tunable, and where the target tissue is located within or adjacent a peripheral nerve.

Referring now to FIG. 10, the placement of the electrode or electrodes 107 in order to deliver a broad spectrum of tunable electrical noise signals to an area within or adjacent target neural tissue, non-neural tissue, or a combination thereof 133 located adjacent or near a peripheral nerve is discussed in more detail. For instance, one or more electrodes 107 can be positioned near or adjacent a peripheral nerve at any location along its length, where the peripheral nerve can run, for instance, down the length of the leg 138 of the patient 116. In the particular embodiment of FIG. 10, the target tissue 133 is located adjacent the sciatic nerve 140, although it is to be understood that neural tissue, non-neural tissue, or a combination thereof can be located adjacent any peripheral nerve in the leg (e.g., the common peroneal nerve 142, the tibial nerve 144, etc.), or any other location in the body. By placing the electrode or electrodes 107 adjacent or near a peripheral nerve, a broad spectrum of tunable electrical noise signals can be delivered to the target neural tissue, non-neural tissue, or a combination thereof 133 to provide therapy to the patient. Specific diseases or conditions that can be treated based on stimulation of a peripheral nerve include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, headache and migraine, cervical neuritis, post-herpetic neuralgia, vertigo, tinnitus, hearing loss and inflammatory pain such as arthritis, irritable bowel pain, overactive bladder, bowel incontinence or constipation, osteoarthritis pain, and fibromyalgia. For example, a broad spectrum of tunable noise signals can be used to stimulate the sacral nerve roots to treat overactive bladder, fecal incontinence, and/or sexual dysfunction. In some embodiments, the electrode(s) may be placed adjacent or near a cranial nerve.

It should be appreciated from the description that the electrode(s) 107 may be placed in particular location in order to treat a particular condition using the tunable noise technologies described herein. For example, in an embodiment, the electrode(s) 107 may be placed within an epidural space between T7 and T12 of a thoracic portion of the patient's spine to treat the patient for spinal lumbar pain. In another embodiment, the electrode(s) 107 may be placed within an epidural space between C2 and T1 of a cervical portion of the patient's spine to treat the patient for spinal cervical pain. In another embodiment, the electrode(s) 107 may be placed within an epidural space between C2 and T8 of the patient's spine to treat angina pain. In another embodiment, the electrode(s) 107 may be placed within an epidural space between C2 and T8 of the patient's spine to treat abdominal pain. In another embodiment, the electrode (s) 107 may be placed within an epidural space between T10 and L5 of the patient's spine to treat peripheral vascular disease. In another embodiment, the electrode(s) 107 may be placed within an epidural space between T7 and T12 in the thoracic spine to treat spinal lumbar pain disorders. In another embodiment, the electrode(s) 107 may be placed within an epidural space between C2 and T1 of a cervical portion of the patient's spine to treat the patient for upper limb ischemia. In another embodiment, the electrode(s) 107 may be placed at or within a dorsal root ganglion of the patient's spin to treat chronic or acute pain. In another embodiment, the electrode(s) 107 may be placed within a sacral portion of the patient's spine to treat urinary or fecal incontinence. In various embodiments, the electrode(s) 107 may be placed near or around the lumbar sympathetic plexus, the celiac sympathetic plexus, the hypogastric sympathetic plexus, or the stellate ganglion to treat chronic or acute pain of the limb, abdomen, pelvic area, or upper extremity, respectively. In another embodiment, the electrode(s) 107 may be placed near or around the patient's brain to treat movement disorders, Parkinson's, pain, psychiatric and/or seizure disorders. In another embodiment, the electrode(s) 107 may be placed near or around the patient's vagus nerve to treat seizure disorders, obesity, pain, or autonomic disorders. In another embodiment, the electrode (s) 107 may be placed near or around a peripheral nerve of the patient to treat acute pain, chronic pain, fecal or urinary incontinence, seizure disorders, movement disorders, obesity, spasticity, and to modulate other unpleasant neurological conditions. In another embodiment, the electrode(s) 107 may be placed near or around the patient's somatic tissue, muscles, connective tissue, or non-neural tissue to treat acute pain, chronic pain, fecal or urinary incontinence, seizure disorders, movement disorders, obesity, spasticity, and to modulate other unpleasant neurological conditions. In another embodiment, the electrode(s) 107 may be placed near or around the patient's visceral tissue or organs, and non-neural tissue to treat acute pain, chronic pain, fecal or urinary incontinence, seizure disorders, movement disorders, obesity, spasticity, and to modulate other unpleasant neurological conditions.

The various components of the systems 50, 100, and 300 described in FIGS. 1-10 may form the portion of a tunable noise control system 400 as described below in more detail in reference to FIG. 12.

Figure 12:
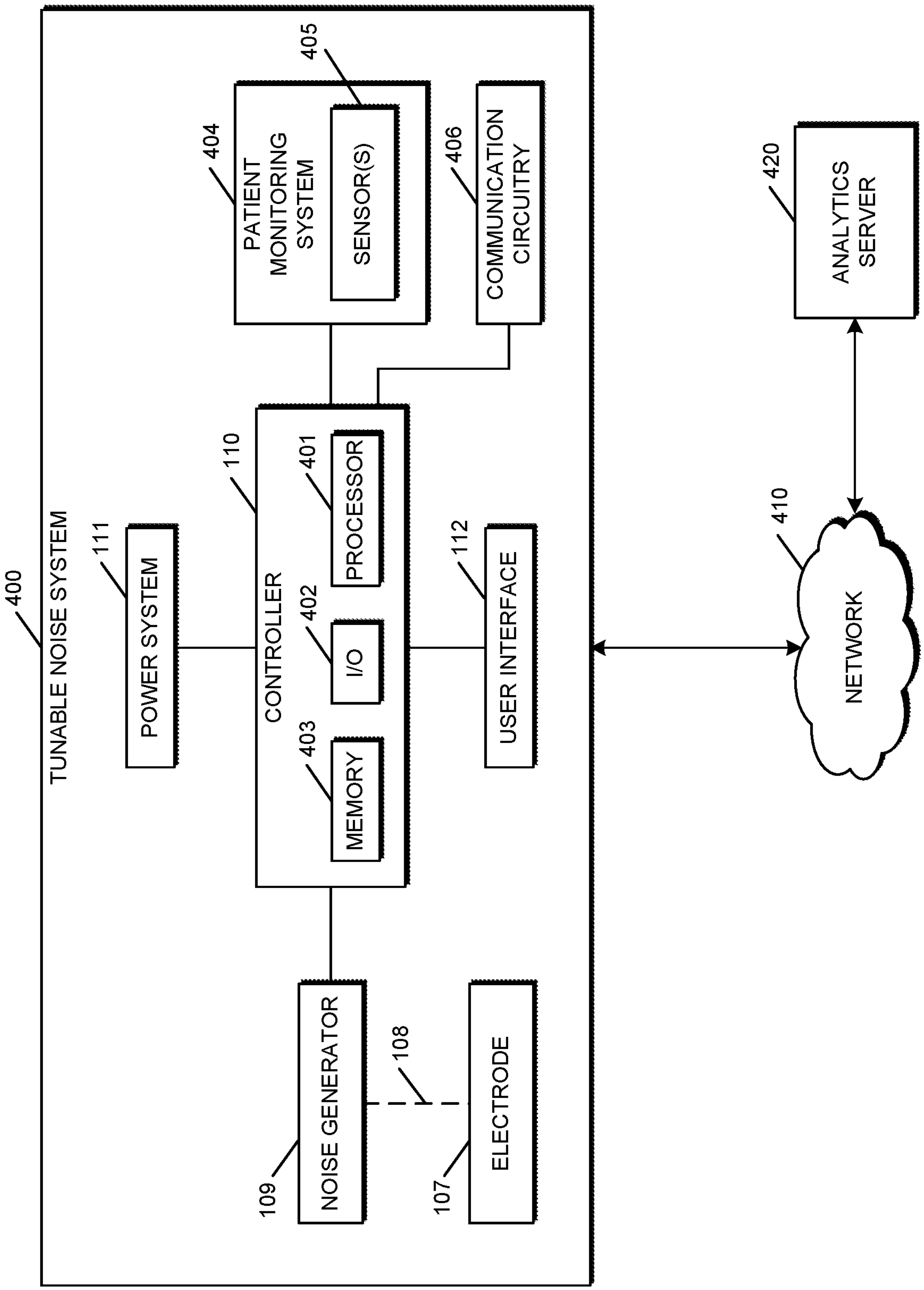
FIG. 12 is a simplified block diagram of at least one embodiment of a tunable noise system for providing therapy to a patient via the application of one or more tunable noise signals.

Referring now to FIG. 12, a simplified block diagram of at least one embodiment of a tunable noise system 400 for providing therapy to a patient via the application of one or more tunable noise signals and otherwise performing the functions described herein is shown. The illustrative tunable noise system 400 includes an electrode 107, a noise generator 109, a controller 110, a power system 111, a user interface 112, a patient monitoring system 404, and a communication circuitry 404. Further, in the illustrative embodiment, the controller 110 includes a processor 401, an input/output ("I/O") subsystem 402, and a memory 403, and the patient monitoring system 404 includes one or more sensors 405. It should be appreciated that one or more of the components of the tunable noise system 400 described herein may be embodied as, or form a portion of, one or more embedded controllers and/or integrated circuits. For example, in some embodiments, the processor 401, the I/O subsystem 402, the memory 403 and/or other components of the tunable noise system 400 may be embodied as, or form a portion of, a microcontroller or SoC (e.g., such as an embodiment in which the controller 110 is a microcontroller). Further, depending on the particular embodiment, the components of the tunable noise system 400 may be closely positioned to one another or spatially distributed (i.e., separated from one another) depending on the particular embodiment. Additionally, although only a single electrode 107, noise generator 109 controller 110, power system 111, user interface 112, patient monitoring system 404, communication circuitry 404, processor 401, I/O subsystem 402, and memory 403 are illustratively shown in FIG. 12, it should be appreciated that a particular tunable noise system 400 may include multiple electrodes 107, noise generators 109 controllers 110, power systems 111, user interfaces 112, patient monitoring systems 404, communication circuitries 404, processors 401, I/O subsystems 402, and/or memories 403 in various embodiments.

One or more electrodes 107 can be used to deliver the broad spectrum of tunable electrical noise signals to the target neural tissue, non-neural tissue, or a combination thereof as described herein. Depending on the particular embodiment, the one or more electrodes 107 can be implantable, percutaneous, or transcutaneous. Further, the one or more electrodes 107 can have a monopolar, bipolar, or multipolar configuration. For example, an electrode 107 used in a bipolar or multi-polar fashion has at least one cathode and one anode in the vicinity of the target neural tissue, non-neural tissue, or a combination thereof, while a monopolar electrode 107 can have a cathode located nearby the target neural tissue, non-neural tissue, or a combination thereof, and a return electrode 107 positioned some distance away. Further, the electrode 107 shape and size, and inter-electrode spacing can be specific to contouring the electrical field surrounding the target neural tissue, non-neural tissue, or a combination thereof, to enable specific therapy to be provided to the target neural tissue, non-neural tissue, or a combination thereof. It should be appreciated that one or more electrodes 107 may be embodied on or electrically coupled to one or more electrical leads 108, which may be connected to the noise generator 109 as described herein.

As shown in the figures, the electrode or electrodes 107 may be connected to an implantable noise generator 109 through an electrical lead 108. Alternatively, in some embodiments, the noise generator 109 can be external and can be wirelessly connected to the electrode or electrodes 107. In some embodiments, the noise generator 109 can be configured to generate and deliver a broad spectrum of tunable electrical noise signals to provide therapy to a patient that can be customized based on patient feedback. As described above, the patient feedback may be based on self-report (e.g., introspection, observations of unwanted sensory- and/or motor activity, autonomic dysfunction, etc.), determined from data generated by sensors measuring physiological outcomes, based on data from artificial intelligence or machine learning systems (e.g., output or feedback data), or based on combinations thereof.

As described herein, white noise is composed of a random signal with equal intensity that exists over all frequencies, giving it a constant power spectral density. That is, if the sample space is infinitely long (i.e. infinite points in time), then the signal will present at all frequencies and a single intensity. At any point in time however, the signal will only be represented as one frequency and one amplitude (e.g., of voltage/current). For the purposes of this disclosure, the white noise stimulation is described herein as a "broad spectrum" of electrical noise signals (see, for example, FIG. 15), and the entire range of possible frequencies is divided into tunable bandwidths (see, for example, FIG. 16). Importantly, as described herein, other colors of noise can be used as the "broad spectrum" of electrical noise signals.

Although the tunable noise technologies are described herein primarily with reference to the use of a single noise generator 109, it should be appreciated that the tunable noise system 400 may utilize multiple noise generators 109 (or multiple noise signal generators) in some embodiments. If only one electrical noise generator 109 is used, then only one signal is delivered to the patient at a particular time. As such, only one frequency band is powered at that time, leaving all others in a period of quiescence. Moreover, the frequency band that receives power is determined in a random fashion. It should be appreciated that, in some embodiments, the use of a single noise generator 109 may maximize the randomness of the therapeutic waveform (needed to reduce neurological tolerance) and/or reduce device power consumption. In such embodiments, it may not, however, allow multiple frequency bands to be powered at the same time, which may be needed to fully maximize interactions between frequency bands.

The use of multiple noise generators 109 (or multiple noise signal generators) enhances the resolution of the noise generator 109 by independently powering some electrical contacts with one signal, and powering other contacts with a different signal, and/or by allowing one waveform to be added to another waveform and delivered through the same set of contacts. Accordingly, a tunable noise system 400 that contains multiple independent noise generators 109 (or noise signal generators) may enable improved control of electrical contacts, may enable improved control of the waveform's randomness, and/or may facilitate interactions between frequency bands (e.g., multi-waveform, physiological, and psychophysical masking).

As described herein, the broad spectrum of tunable electrical noise signals (e.g., singular signal or plural signals, depending on the particular embodiment) generated by the noise generator 109 and applied to the target neural tissue, non-neural tissue, or a combination thereof of the patient can include Gaussian noise, white noise, pink noise, red (Brownian) noise, grey noise, or any combination thereof in order to provide the desired therapy to the patient.

A Gaussian noise signal includes a statistical noise having a probability density function (PDF) equal to that of the normal distribution, which is also known as the Gaussian distribution. In other words, the values that the noise can take on are Gaussian-distributed.

A white noise electrical signal refers to a signal having a flat frequency spectrum when plotted as a linear function of frequency and can thus be described as a random signal with a constant power spectral density (energy or power per Hz). In other words, the signal has equal power in any band of a given bandwidth (power spectral density) when the bandwidth is measured in Hz. For example, with a white noise signal, the range of frequencies between 40 Hz and 60 Hz contains the same amount of power as the range between 400 Hz and 420 Hz, since both intervals are 20 Hz wide.

A pink noise signal has a frequency spectrum that is linear in logarithmic space. As such, it has equal power in bands that are proportionally wide. This means that pink noise would have equal power in the frequency range from 40 to 60 Hz as in the frequency range from 4000 to 6000 Hz. Also called "1/f noise," pink noise is characterized by a frequency spectrum where the power spectral density (energy or power per Hz) is inversely proportional to the frequency of the signal. Since there are an infinite number of logarithmic bands at both the low frequency (DC) and high frequency ends of the spectrum, any finite energy spectrum must have less energy than pink noise at both ends. Pink noise is the only power-law spectral density that has this property: all steeper power-law spectra are finite if integrated to the high-frequency end, and all flatter power-law spectra are finite if integrated to the DC, low-frequency limit.

A red or Brownian noise signal is based on the concept of Brownian motion and can also be referred to as "random walk noise." Red or Brownian noise has a power spectral density that is inversely proportional to $f^2$, meaning it has more energy at lower frequencies, even more so than pink noise.

A grey noise signal exhibits a frequency spectrum such that the power spectral density is equal at all frequencies.

Regardless of the particular type or combination of electrical noise signals utilized, the broad spectrum of electrical noise signals can be tuned, such that the energy contained within a particular frequency band, and for all frequency bands of energy delivered to the tissue, can be adjusted to best treat the patient as described herein. In illustrative embodiments, the broad spectrum of tunable electrical noise energy can be adjusted to deliver electrical noise with intensities ranging from about 0.01 volts (V) to about 200 V, such as from about 0.1 V to about 100 V, such as from about 0.5 V to about 50 V, for all or each frequency band included in the spectrum. In illustrative embodiments, the spectrum of electrical noise includes frequencies ranging from about 0.001 hertz (Hz) (e.g., approximately 0 Hz) to about 500 kilohertz (kHz), such as from about 0.01 Hz to about 250 kHz, such as from about 0.05 Hz to about 200 kHz, and is composed of tunable frequency bands ranging from about 1 Hz (or approximately 0 Hz) to about 100 kHz, such as from about 5 Hz to about 75 kHz, such as from about 10 Hz to about 50 kHz.

Figure 23:
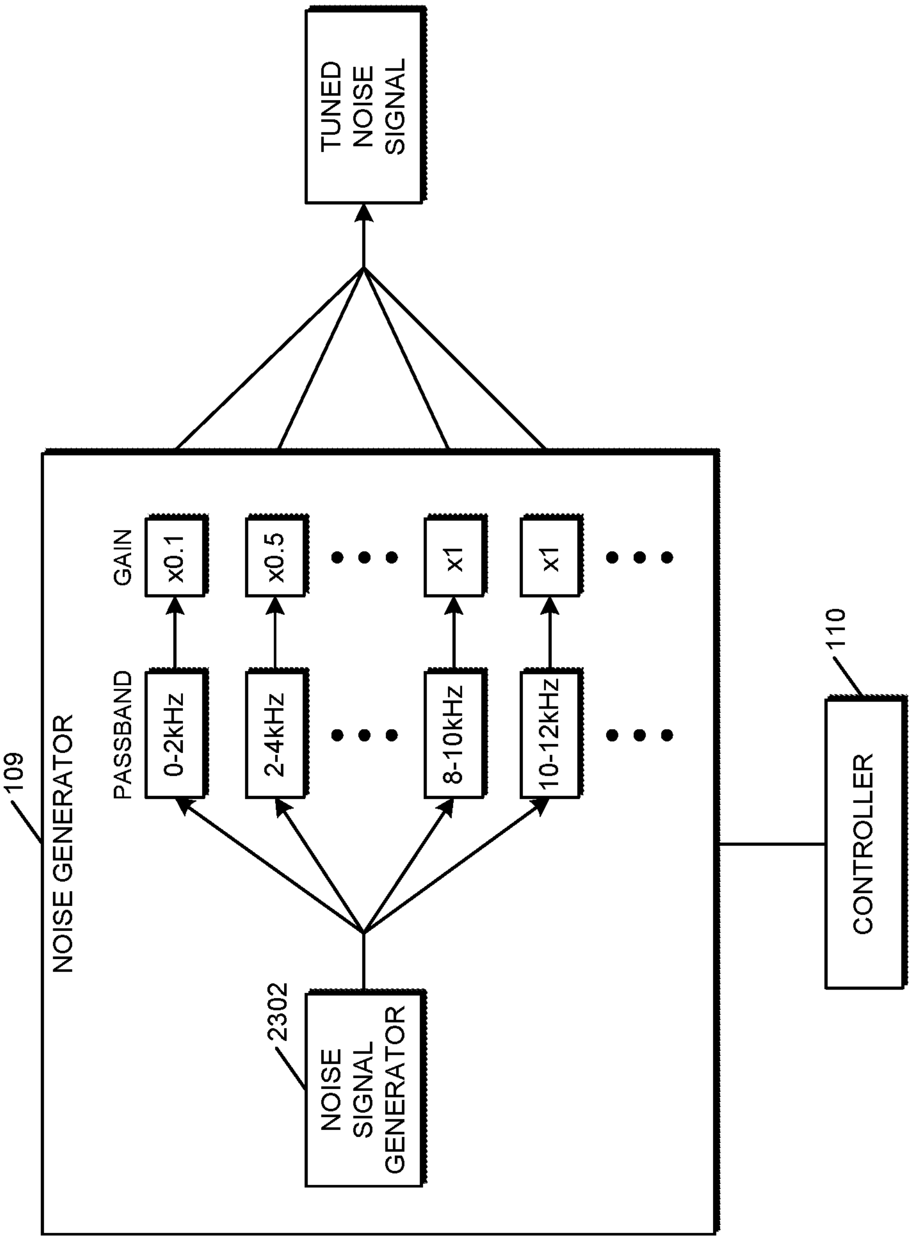
FIGS. 23-25 are simplified block diagrams of various embodiments of a noise generator for use in a tunable noise system for providing therapy to a patient via the application of one or more tunable noise signals.
Figure 24:
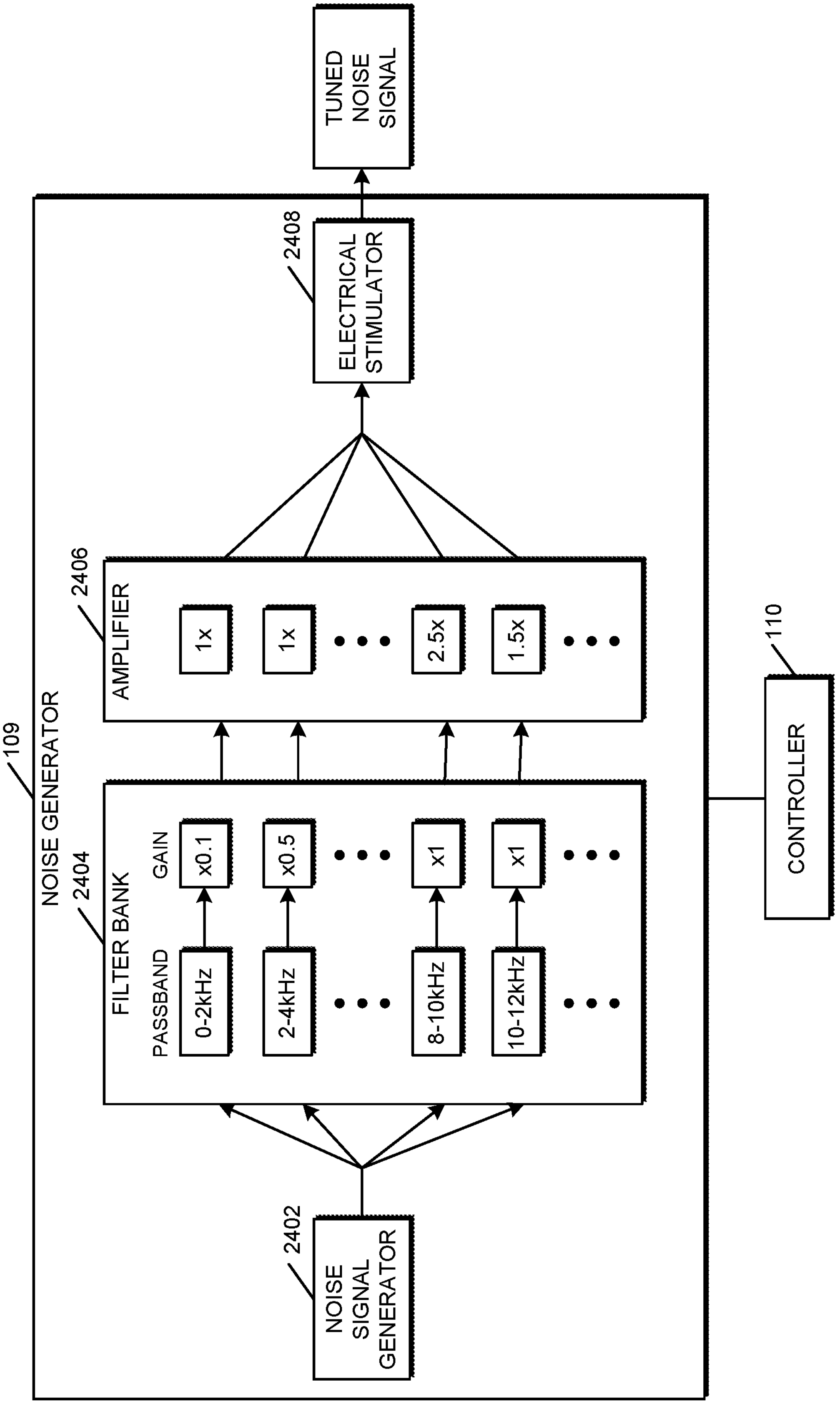
Figure 25:
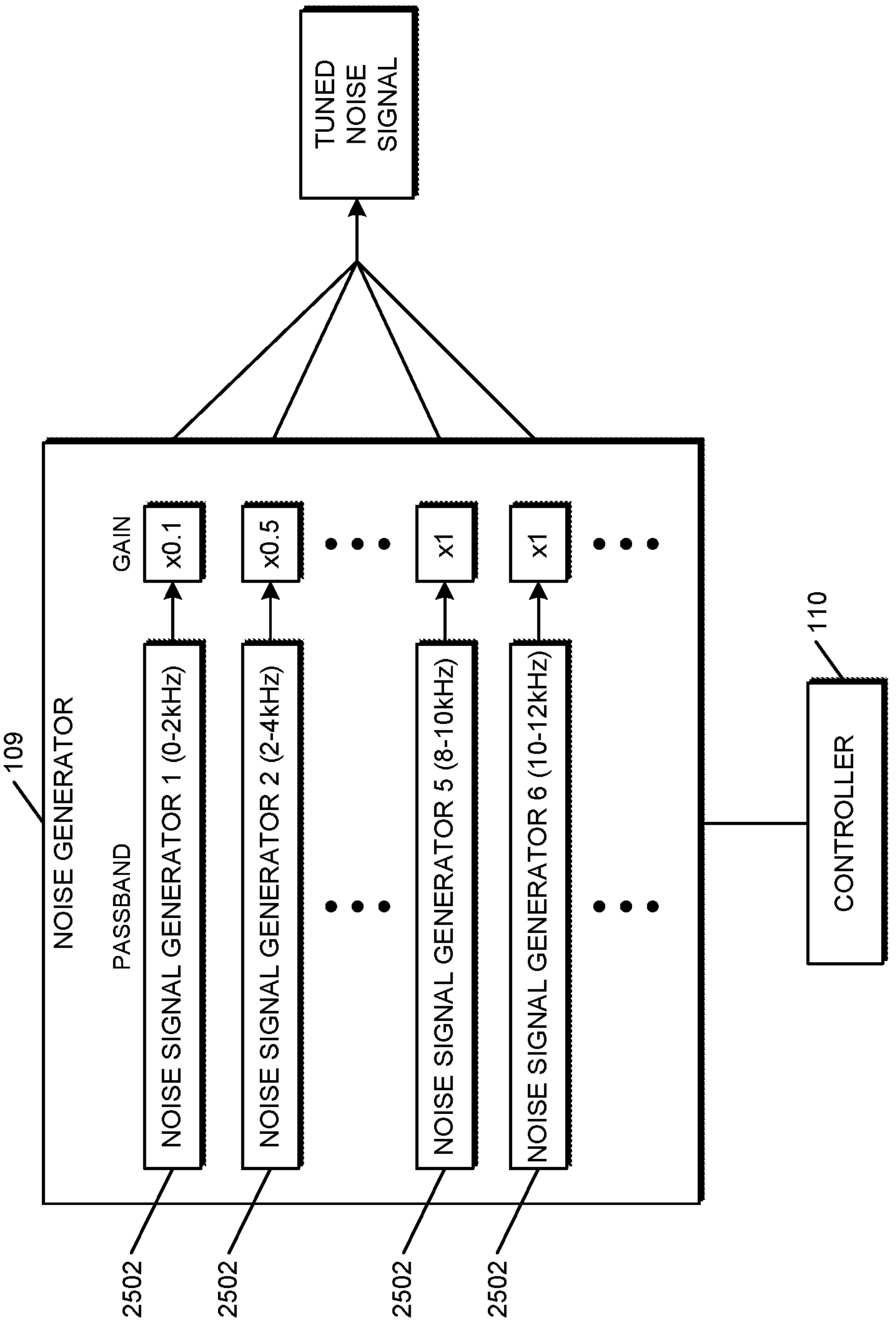

Exemplary embodiments of a noise generator 109 for use in the tunable noise system 500 are shown and described in reference to FIGS. 23-25. Referring now to FIG. 23, in the illustrative embodiment, a noise signal generator 2302 generates a broad spectrum electrical noise signal. It should be appreciated that the broad spectrum electrical noise signal may be generated using any suitable technique. For example, in some embodiments, the noise signal generator 2302 may generate the electrical noise signal using subtractive synthesis, additive synthesis, component modeling synthesis, wavetable synthesis, vector synthesis, linear arithmetic synthesis, phase distortion synthesis, frequency modulation synthesis, sample-based synthesis, random number generation, and/or another suitable technique. As shown, the generated electrical noise signal is passed to a filter bank that includes one or more bandpass filters. In the illustrative embodiment, the cumulative passband frequencies of the bandpass filters cover the entire range of the noise signal frequency range. It should be appreciated that the controller 110 controls the filter bank to modify each bandpass filter's operational settings including, for example, center frequency, cutoff frequencies (e.g., half-power points), attenuation rate (filter-order), overall attenuation of the passband, and/or other operational settings of the filter. The signals outputted from each bandpass filter may be passed through an amplifier, which may be controlled by the controller 110 to apply gain to the corresponding filtered signals, and compiled into a single electrical waveform (e.g., the tuned noise signal). As described herein, the tuned noise signal may be delivered to the patient through the electrode(s) 107.

Referring now to FIG. 24, in the illustrative embodiment, a noise signal generator 2402 similar to the noise signal generator 2402 of FIG. 23 generates a broad spectrum electrical noise signal using a suitable technique. As shown, the generated electrical noise signal is passed to a filter bank 2404 that includes one or more bandpass filters. In the illustrative embodiment, the cumulative passband frequencies of the bandpass filters cover the entire range of the noise signal frequency range. As shown, gain may be applied to one or more of the signals outputted from the bandpass filters. It should be appreciated that the controller 110 controls the filter bank 2404 to modify each of the bandpass filter's operational settings, gain, and/or other signal characteristics. In some embodiments, the filter bank 2404 may include one or more band-reject filters or a combination of bandpass and band-reject filters. The signals outputted from the filter bank 2404 may be passed through an amplifier 2406 that applies a corresponding amount of amplification to each of the signals, and then passed to an electrical stimulator 2408. Depending on the particular embodiment, the electrical stimulator 2408 may receive multiple signals from the amplifier 2406 or a single combined signal. The electrical stimulator 2408 may be embodied as an isolated electrical generator that converts the inputted waveform(s) into a safe electrical stimulation that can be delivered to the patient through the electrode(s) 107. It should be appreciated that one or more of the noise signal generator 2402, the filter bank 2404, the amplifier 2406, and/or the electrical stimulator 2408 may be controlled by the controller 110.

Referring now to FIG. 25, a noise generator 109 including a plurality of noise signal generators 2502 is shown. As described herein, each noise signal generator 2502 may be configured to deliver electrical noise within a narrow frequency band, and multiple bands may be used to cover the therapeutic frequency range. It should be appreciated that the controller 110 may control various aspects of the noise generator 109 including, for example, the center frequency, bandwidth, and/or power (e.g., via controlling the amplitude of voltage and/or current) of each frequency band delivered by each noise signal generator 2502. It should be appreciated that the signals may be further filtered and/or amplified in a manner similar to that described in reference to FIGS. 23-24.

The power supply, power source, or power system 111 is configured to supply power to the controller 110 and/or other components of the tunable noise system 400. In some embodiments, the power system 110 is an independent, untethered, and portable power source configured to supply power to the tunable noise system 400 to perform the various functions described herein. For example, the power system 111 may include one or more batteries, battery packs, capacitors, super capacitors, solar cells, and/or other power supplies. Depending on the particular embodiment, the power system 111 may or may not be rechargeable. In other embodiments, the power system 111 may be line powered via AC mains and/or another suitable power source. It should be appreciated that the power system 111 can include both external and internal portions, where the internal portion of the power system can include a battery, such as a lithium battery, and the external portion of the power system 111 can be plugged into a wall and used to recharge the battery as needed. In such embodiments, the external portion of the power system 111 can transmit power to the noise generator 109 as directed by the controller 110 via RF signals/electromagnetic induction, or power can be transmitted to the noise generator 109 via the battery in the internal portion of the power system 111. Further, the external portion of the power system 111 can be used to recharge the battery in the internal portion of the power system 111.

The user interface 112 may be embodied as any one or more devices or components that allow a user to interact with the tunable noise system 400. For example, in some embodiments, the user interface 112 can be in the form of a computer that interacts with the controller 110 and is powered by a power system 111. In particular, in some embodiments, the computer can operate software designed to record signals passed from the controller 110, and to drive the controller's output. Possible software packages include Cambridge Electronic Design's (UK) SPIKE program. The software can be programmable and can record and analyze electrophysiological signals, as well as direct the controller 110 to deliver the broad spectrum of tunable electrical noise signals described herein. Further, in some embodiments, the user interface 112 may include one or more peripheral devices such as, for example, a keyboard, mouse, display, status indicator, diagnostic tool, speaker, microphone, and/or one or more other suitable peripheral devices.

In some embodiments, the tunable noise system 400 may include a patient monitoring system 404. In such embodiments, the patient monitoring system 404 can acquire, amplify/attenuate, and filter physiological signals and then output them to the controller 110. It should be appreciated that the patient monitoring system 404 may include one or more sensors 405. The sensors 405 are configured to generate sensor data (e.g., by virtue of one or more signals), which may be interpreted by the controller 110 (e.g., the processor 401) to determine one or more characteristics associated with the patient and/or the tunable noise system 400. By way of example, the sensors 405 may detect various characteristics of the physical environment of the tunable noise system 400 (internal and/or external) and/or other suitable characteristics. In various embodiments, the sensors 405 may be embodied as, or otherwise include, environmental sensors, inertial sensors, proximity sensors, optical sensors, electromagnetic sensors, audio sensors, pressure sensors, flow meters, temperature sensors, chemical sensors, biopotential electrodes, motion sensors, piezoelectric sensors, cameras, and/or other types of sensors. Of course, the tunable noise system 400 may also include components and/or devices configured to facilitate the use of the sensors 405. For example, in some embodiments, the patient monitoring system 404 may include a heart-rate monitor to collect electrocardiogram signals and/or a muscle activity monitor to collect electromyography signals. The heart-rate monitor can include ECG electrodes coupled with an alternating current (AC) amplifier, and the muscle activity monitor can include EMG electrodes coupled with an AC amplifier. Other types of transducers may also be used in other embodiments. As described, physiological signals obtained with the patient monitoring system 404 may be passed through an AC signal amplifier/conditioner. One possible amplifier/conditioner is a Model LP511 AC amplifier available from Grass Technologies, a subsidiary of Astro-Med, Inc., West Warwick, Rhode Island, USA.

The communication circuitry 406 may be embodied as any communication circuitry, transceiver, device, or collection thereof, capable of enabling communications between the tunable noise system 400 and other remote devices. The communication circuitry 406 may be configured to use any one or more wired and/or wireless communication technologies and associated protocols. For example, in some embodiments, the illustrative tunable noise system 400 may be configured to communicate via Wi-Fi (e.g., infrastructure or ad hoc mode), Wi-Fi Direct, Bluetooth (including Bluetooth Low Energy (BLE)), Zigbee, Z-wave, Near Field Communication (NFC), IEEE 802.15, and/or other suitable wireless communication protocol(s). Further, in some embodiments, the tunable noise system 400 may be configured to communicate via Ethernet, Power over Ethernet (PoE), serial communication links, power line communication, and/or another suitable wired communication mechanism.

The controller 110 may be embodied as any type of controller or control system capable of performing the functions described herein. In the illustrative embodiment, the controller 110 can record electrical noise signal data as well as digital information from the patient monitoring system 404, and can generate electrical noise signal and digital outputs simultaneously for real-time control of the noise generator 109 based on feedback received from the patient after transmission of the broad spectrum of tunable electrical noise signals. The controller 110 may have onboard memory to facilitate high speed data capture, independent waveform sample rates, and on-line analysis. An exemplary controller 110 may be a POWER 1401 data-acquisition interface unit available from Cambridge Electronic Design (UK).

As shown, in some embodiments, the controller 110 includes a processor 401, an I/O subsystem 402, and memory 403.

The processor 401 may be embodied as any type of processor(s) capable of performing the functions described herein. In particular, the processor 401 may be embodied as one or more single or multi-core processors, microcontrollers, or other processor or processing/controlling circuits. For example, in some embodiments, the processor 401 may include or be embodied as an arithmetic logic unit (ALU), central processing unit (CPU), digital signal processor (DSP), and/or another suitable processor(s). The processor 401 may be a programmable type, a dedicated hardwired state machine, or a combination thereof. One or more processors 401 with multiple processing units may utilize distributed, pipelined, and/or parallel processing in various embodiments. Further, the processor 401 may be dedicated to performance of just the operations described herein, or may be utilized in one or more additional applications. In the illustrative embodiment, the processor 401 is of a programmable variety that executes algorithms and/or processes data in accordance with operating logic as defined by programming instructions (such as software or firmware) stored in the memory 403. Additionally or alternatively, the operating logic for the processor 401 may be at least partially defined by hardwired logic or other hardware. Further, the processor 401 may include one or more components of any type suitable to process the signals received from input/output devices or from other components or devices and to provide desired output signals. Such components may include digital circuitry, analog circuitry, or a combination thereof.

The memory 403 may be of one or more types of non-transitory computer-readable media, such as a solid-state memory, electromagnetic memory, optical memory, or a combination thereof. Furthermore, the memory 403 may be volatile and/or nonvolatile and, in some embodiments, some or all of the memory 403 may be of a portable variety, such as a disk, tape, memory stick, cartridge, and/or other suitable portable memory. In operation, the memory 403 may store various data and software used during operation of the tunable noise system 400 such as operating systems (e.g., real-time operating systems (RTOS)), applications, programs, libraries, and drivers. The memory 403 is communicatively coupled to the processor 401 via the I/O subsystem 402, which may be embodied as circuitry and/or components to facilitate input/output operations with the processor 401, the memory 403, and other components of the tunable noise system 400. For example, the I/O subsystem 402 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. Depending on the particular embodiment, the memory 403 may be included with the processor 401 and/or coupled to the processor 401 depending on the particular embodiment. For example, in some embodiments, the processor 401, the I/O subsystem 402, the memory 403, and/or other components of the tunable noise system 400 may form a portion of a system-on-a-chip (SoC) and be incorporated on a single integrated circuit chip.

As shown in FIG. 12, in some embodiments, the tunable noise system 400 or a portion thereof (e.g., the controller 110) may be configured to communicate with an analytics server 420 and/or other remote computing device via a network 410. For example, in some embodiments, the tunable noise system 400 may transmit patient data (e.g., including optimal noise signature), sensor data, and/or other data to the analytics server 420 for leveraging artificial intelligence, machine learning, and/or other technologies for pattern identification and/or decision-making.

The network 410 may be embodied as any type of communication network capable of facilitating communication between the tunable noise system 400 and the analytics server 420 and/or other remote devices. As such, the network 410 may include one or more networks, routers, switches, computers, and/or other intervening devices. For example, the network 410 may be embodied as or otherwise include one or more cellular networks, telephone networks, local or wide area networks, publicly available global networks (e.g., the Internet), ad hoc networks, short-range communication links, or a combination thereof.

The analytics server 420 may be embodied as any type of device(s) capable of performing the functions described herein. It should be appreciated that the efficacy of neuromodulation technologies is affected by continuously changing treatment variables. Treatment variables may be device-specific (e.g., lead migration and impedance changes, stimulation paradigm, etc.), physiological (e.g., neurological conditioning or tolerance, scar tissue formation, plasticity, etc.), psychological (e.g., depression, etc.), disease state specific (e.g., progression, improvement, etc.) and/or patient dependent (e.g., height, weight, age, race, etc.). Moreover, these treatment variables generally change with time and may interact (stim*time interaction, long-term physiological changes, etc.).

The tunable noise stimulation system described herein can accommodate for the changing treatment variables by offering a broad range of stimulation frequencies and intensities that are delivered in a random fashion and are tuned by the patient to best treat the patient's condition. The term "tunable noise signature" may be used herein to describe the optimal (or best known) stimulation paradigm (stimulation power/frequency–power spectrum) used by a patient to maximize treatment efficacy.

In some embodiments, one or more artificial intelligence and/or machine learning algorithms/technologies may be leveraged to help patients determine and maintain the proper tunable noise signature throughout the life of the patients' respective treatments. Accordingly, it should be appreciated that the tunable noise system 400 may be configured to export the tunable noise signature (e.g., after identifying the signature) and various treatment variables for one or more patients (e.g., each patient) to the analytics server 420 and/or another system/device. In some embodiments, the analytics server 420 may collect the tunable noise signature and treatment variables from many tunable noise systems 400, and use artificially intelligent processes (e.g., machine learning, deep learning, neural networks, and/or other technologies) to predict a novel tunable noise signature. The predicted tunable noise signature (re-tuned signature) may then be transmitted back to one or more tunable noise systems 400 to be installed and trailed by one or more patients. Further, in some embodiments, the patient may then accept or modify the stimulation paradigm as necessary to best treat their condition in a manner similar to the tuning of electrical noise signals otherwise described herein. It should be appreciated that the prediction may help to program the tunable noise system 400 initially, may be used over time to optimize treatment, and/or may be used to re-capture a failing therapy. Moreover, in some embodiments, the artificial intelligence programs may also be used to predict entirely new treatments for novel indications.

In some embodiments, the inputs for a neural network or other machine learning algorithm used by the analytics server 420 may include one or more of tuned noise signatures, patient information, patient demographics, diagnosis information, electrode positioning, patient sensations, measures of treatment efficacy and/or outcomes (e.g., Pain Rating Scale scores), time of day, duration of treatment, time elapsed since start of treatment plan, and/or other machine learning model inputs. Further, in various embodiments, the analytics server 420 may utilize any machine learning and/or artificial intelligence algorithm for performing the functions described herein. For example, in some embodiments, the analytics server 420 may utilize one or more neural network algorithms, regression algorithms, instance-based algorithms, regularization algorithms, decision tree algorithms, Bayesian algorithms, clustering algorithms, association rule learning algorithms, deep learning algorithms, dimensionality reduction algorithms, and/or other suitable machine learning algorithms, techniques, and/or mechanisms.

It should be further appreciated that, although the analytics server 420 is described herein as a computing device outside of a cloud computing environment, in other embodiments, the analytics server 420 may be embodied as a cloud-based device or collection of devices within a cloud computing environment. Further, in cloud-based embodiments, the analytics server 420 may be embodied as a server-ambiguous computing solution, for example, that executes a plurality of instructions on-demand, contains logic to execute instructions only when prompted by a particular activity/trigger, and does not consume computing resources when not in use. That is, the analytics server 420 may be embodied as a virtual computing environment residing "on" a computing system (e.g., a distributed network of devices) in which various virtual functions (e.g., Lambda functions, Azure functions, Google cloud functions, and/or other suitable virtual functions) may be executed corresponding with the functions of the analytics server 420 described herein. For example, when an event occurs (e.g., data is transferred to the analytics server 420 for handling), the virtual computing environment may be communicated with (e.g., via a request to an API of the virtual computing environment), whereby the API may route the request to the correct virtual function (e.g., a particular server-ambiguous computing resource) based on a set of rules. For example, when a request for the transmission of data is made (e.g., via an appropriate user interface to the analytics server 420), the appropriate virtual function(s) may be executed to perform the actions before eliminating the instance of the virtual function(s).

Figure 13:
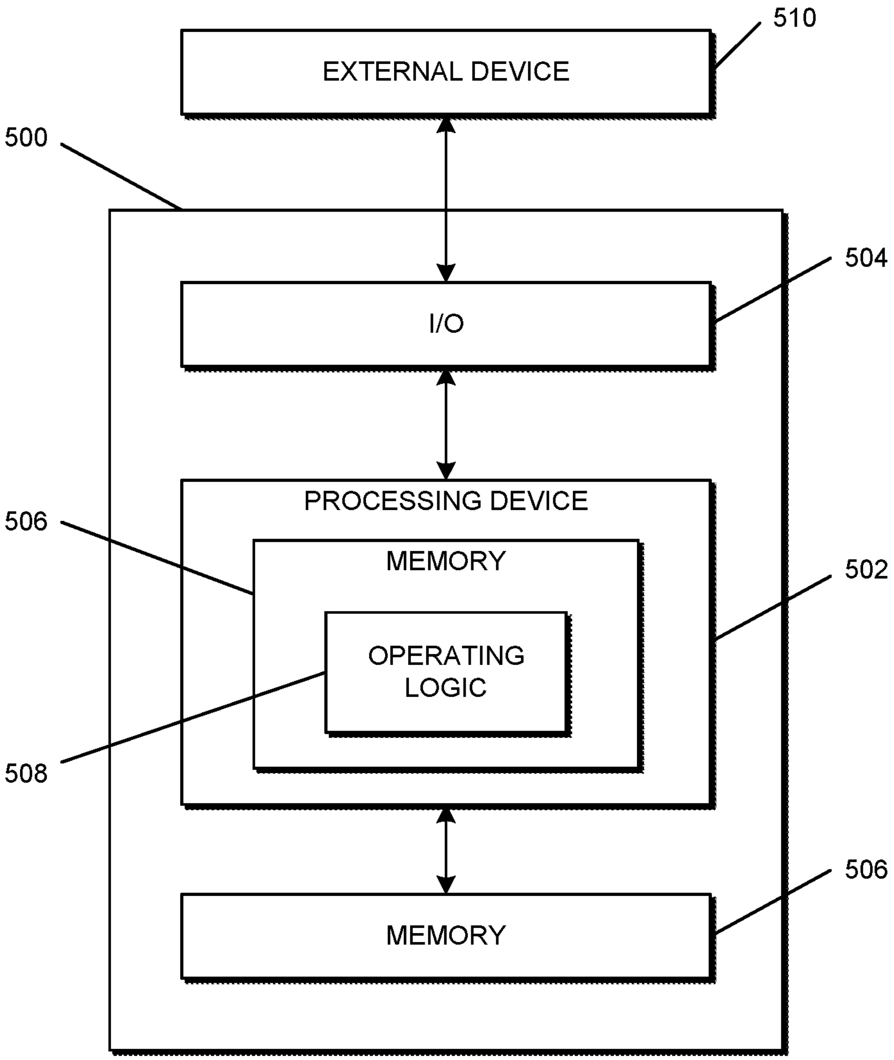
FIG. 13 is a simplified block diagram of at least one embodiment of a computing system.

Referring now to FIG. 13, a simplified block diagram of at least one embodiment of a computing device 500 is shown. The illustrative computing device 500 depicts at least one embodiment of a server that may be utilized in connection with the analytics server 420 illustrated in FIG. 12 and/or other devices in communication with the tunable noise system 400. Depending on the particular embodiment, the computing device 500 may be embodied as a server, desktop computer, laptop computer, tablet computer, notebook, netbook, Ultrabook™ mobile computing device, cellular phone, smartphone, wearable computing device, personal digital assistant, Internet of Things (IoT) device, processing system, router, gateway, and/or any other computing, processing, and/or communication device capable of performing the functions described herein.

The computing device 500 includes a processing device 502 that executes algorithms and/or processes data in accordance with operating logic 508, an input/output device 504 that enables communication between the computing device 500 and one or more external devices 510, and memory 506 which stores, for example, data received from the external device 510 via the input/output device 504.

The input/output device 504 allows the computing device 500 to communicate with the external device 510. For example, the input/output device 504 may include a transceiver, a network adapter, a network card, an interface, one or more communication ports (e.g., a USB port, serial port, parallel port, an analog port, a digital port, VGA, DVI, HDMI, FireWire, CAT 5, or any other type of communication port or interface), and/or other communication circuitry. Communication circuitry of the computing device 500 may be configured to use any one or more communication technologies (e.g., wireless or wired communications) and associated protocols (e.g., Ethernet, Bluetooth®, Wi-Fi®, WiMAX, etc.) to effect such communication depending on the particular computing device 500. The input/output device 504 may include hardware, software, and/or firmware suitable for performing the techniques described herein.

The external device 510 may be any type of device that allows data to be inputted or outputted from the computing device 500. For example, in various embodiments, the external device 510 may be embodied as the analytics server 420 and/or the tunable noise system 400. Further, in some embodiments, the external device 510 may be embodied as another computing device, switch, diagnostic tool, controller, printer, display, alarm, peripheral device (e.g., keyboard, mouse, touch screen display, etc.), and/or any other computing, processing, and/or communication device capable of performing the functions described herein. Furthermore, in some embodiments, it should be appreciated that the external device 510 may be integrated into the computing device 500.

The processing device 502 may be embodied as any type of processor(s) capable of performing the functions described herein. In particular, the processing device 502 may be embodied as one or more single or multi-core processors, microcontrollers, or other processor or processing/controlling circuits. For example, in some embodiments, the processing device 502 may include or be embodied as an arithmetic logic unit (ALU), central processing unit (CPU), digital signal processor (DSP), and/or another suitable processor(s). The processing device 502 may be a programmable type, a dedicated hardwired state machine, or a combination thereof. Processing devices 502 with multiple processing units may utilize distributed, pipelined, and/or parallel processing in various embodiments. Further, the processing device 502 may be dedicated to performance of just the operations described herein, or may be utilized in one or more additional applications. In the illustrative embodiment, the processing device 502 is programmable and executes algorithms and/or processes data in accordance with operating logic 508 as defined by programming instructions (such as software or firmware) stored in memory 506. Additionally or alternatively, the operating logic 508 for processing device 502 may be at least partially defined by hardwired logic or other hardware. Further, the processing device 502 may include one or more components of any type suitable to process the signals received from input/output device 504 or from other components or devices and to provide desired output signals. Such components may include digital circuitry, analog circuitry, or a combination thereof.

The memory 506 may be of one or more types of non-transitory computer-readable media, such as a solid-state memory, electromagnetic memory, optical memory, or a combination thereof. Furthermore, the memory 506 may be volatile and/or nonvolatile and, in some embodiments, some or all of the memory 506 may be of a portable type, such as a disk, tape, memory stick, cartridge, and/or other suitable portable memory. In operation, the memory 506 may store various data and software used during operation of the computing device 500 such as operating systems, applications, programs, libraries, and drivers. It should be appreciated that the memory 506 may store data that is manipulated by the operating logic 508 of processing device 502, such as, for example, data representative of signals received from and/or sent to the input/output device 504 in addition to or in lieu of storing programming instructions defining operating logic 508. As shown in FIG. 13, the memory 506 may be included with the processing device 502 and/or coupled to the processing device 502 depending on the particular embodiment. For example, in some embodiments, the processing device 502, the memory 506, and/or other components of the computing device 500 may form a portion of a system-on-a-chip (SoC) and be incorporated on a single integrated circuit chip.

In some embodiments, various components of the computing device 500 (e.g., the processing device 502 and the memory 506) may be communicatively coupled via an input/output subsystem, which may be embodied as circuitry and/or components to facilitate input/output operations with the processing device 502, the memory 506, and other components of the computing device 500. For example, the input/output subsystem may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations.

The computing device 500 may include other or additional components, such as those commonly found in a typical computing device (e.g., various input/output devices and/or other components), in other embodiments. It should be further appreciated that one or more of the components of the computing device 500 described herein may be distributed across multiple computing devices. In other words, the techniques described herein may be employed by a computing system that includes one or more computing devices. Additionally, although only a single processing device 502, I/O device 504, and memory 506 are illustratively shown in FIG. 13, it should be appreciated that a particular computing device 500 may include multiple processing devices 502, I/O devices 504, and/or memories 506 in other embodiments. Further, in some embodiments, more than one external device 510 may be in communication with the computing device 500.

Figure 15:
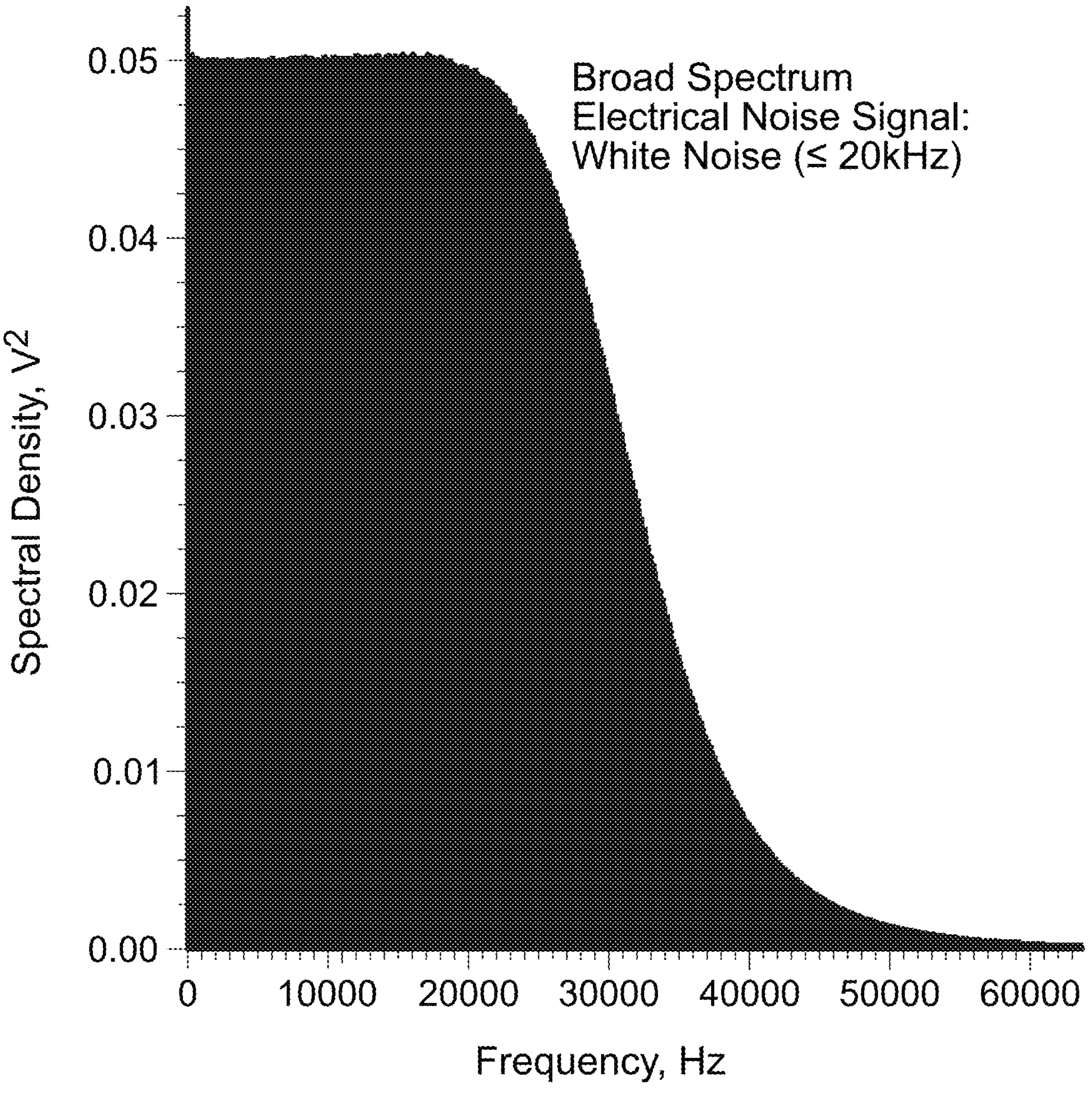
FIG. 15 is a graph of a power spectrum for a broad spectrum electrical noise signal.
Figure 16:
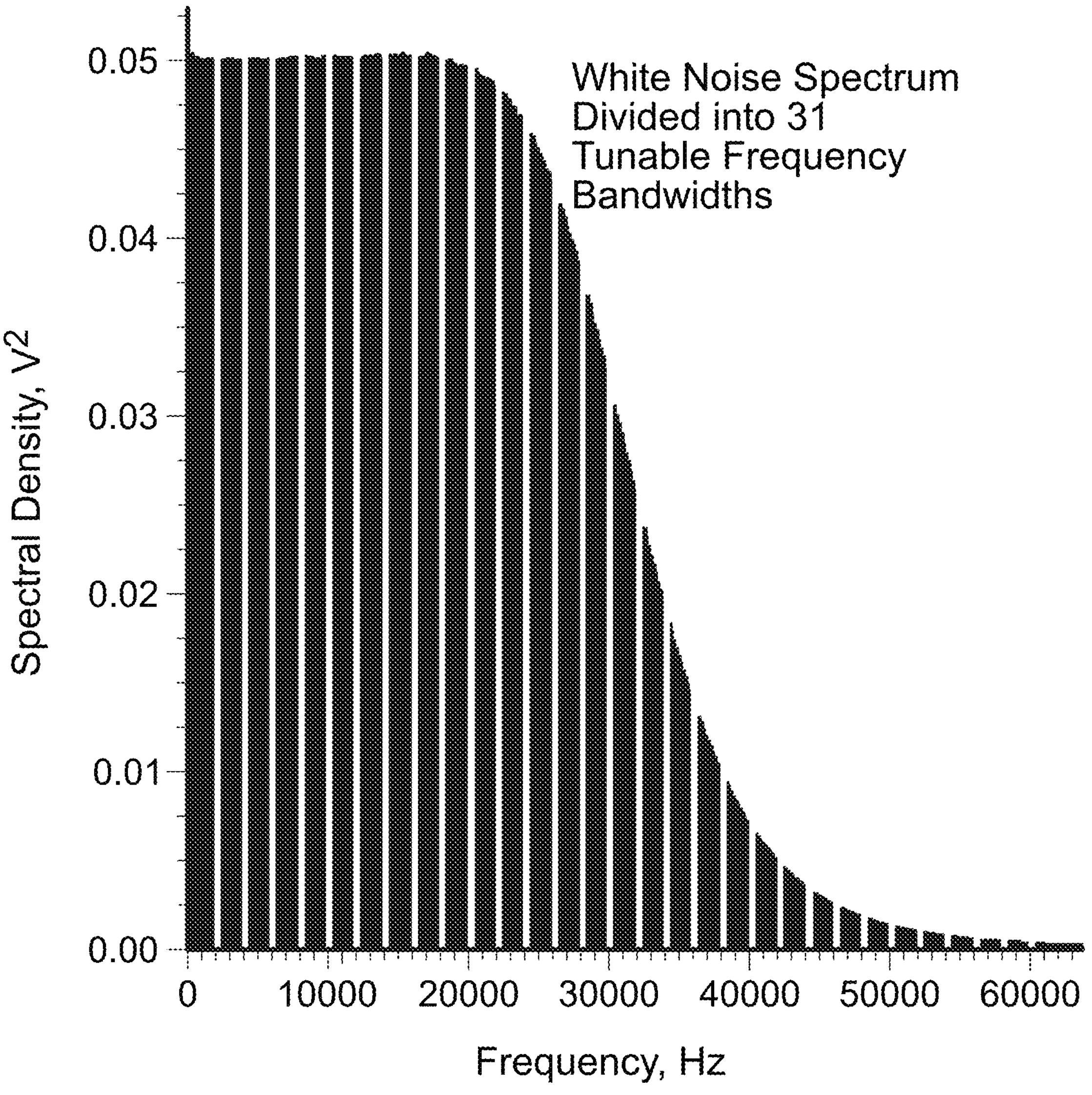
FIG. 16 is a graph of the power spectrum for the broad spectrum electrical noise signal of FIG. 15 partitioned into discrete frequency bands.

In addition to the systems discussed above, the technologies described herein also encompasses a method for providing therapy to a patient that is customizable based on the particular circumstances present at the time the therapy is provided. For instance, after positioning one or more electrodes adjacent the target neural tissue, non-neural tissue, or a combination thereof (e.g., within or adjacent the patient's brain or spinal cord, a dorsal root ganglion, a sympathetic chain ganglion, or a peripheral nerve), the electrode(s) 107 can be electrically connected to an implantable noise generator 109 via a lead 108 or to an external noise generator 109 wirelessly. Then, a user interface 112 and controller 110 can be configured to deliver a broad spectrum of tunable electrical noise signals to provide therapy to the patient. The broad spectrum of electrical noise signals is divided into frequency bands, for example, as shown in FIGS. 15-16. Each frequency band can be independently tuned, such that the energy contained within a particular frequency band, and for all frequency bands of energy delivered to the tissue, can be adjusted to best treat the patient. The broad spectrum of tunable electrical noise energy can be adjusted to deliver electrical noise with intensities ranging from about 0.01 volts (V) to about 200 V, such as from about 0.1 V to about 100 V, such as from about 0.5 V to about 50 V, for all or each frequency band included in the spectrum. The spectrum of electrical noise includes frequencies ranging from about 0.001 hertz (Hz) to about 500 kilohertz (kHz), such as from about 0.01 Hz to about 250 kHz, such as from about 0.05 Hz to about 200 kHz, and is composed of tunable frequency bands ranging from about 1 Hz to about 100 kHz, such as from about 5 Hz to about 75 kHz, such as from about 10 Hz to about 50 kHz.

After the broad spectrum of tunable electrical noise signals is delivered, patient feedback can be used to optimize the therapy provided to the patient. For example, in one particular embodiment, the broad spectrum of electrical noise signals can be tuned based on patient feedback by adjusting energy contained within a frequency band, while in another embodiment, the broad spectrum of electrical noise signals can be tuned based on patient feedback by adjusting a phase component of the broad spectrum. For example, one or more electrodes can be implanted, inserted percutaneously, or positioned transcutaneously such that the electrodes are nearby the target neural tissue, non-neural tissue and combination thereof as necessary to treat their disease or syndrome. A noise generator can then be instructed to deliver a broad spectrum of electrical noise signals through the one or more electrodes. The patient and/or caregiver can then program the optimal stimulation waveform by operating a controller. The controller can tune the waveform associated with the broad spectrum of electrical noise signals being delivered to the patient by adjusting energy levels within a particular frequency band, and for all frequency bands delivered, to best treat the patient.

Figure 14:
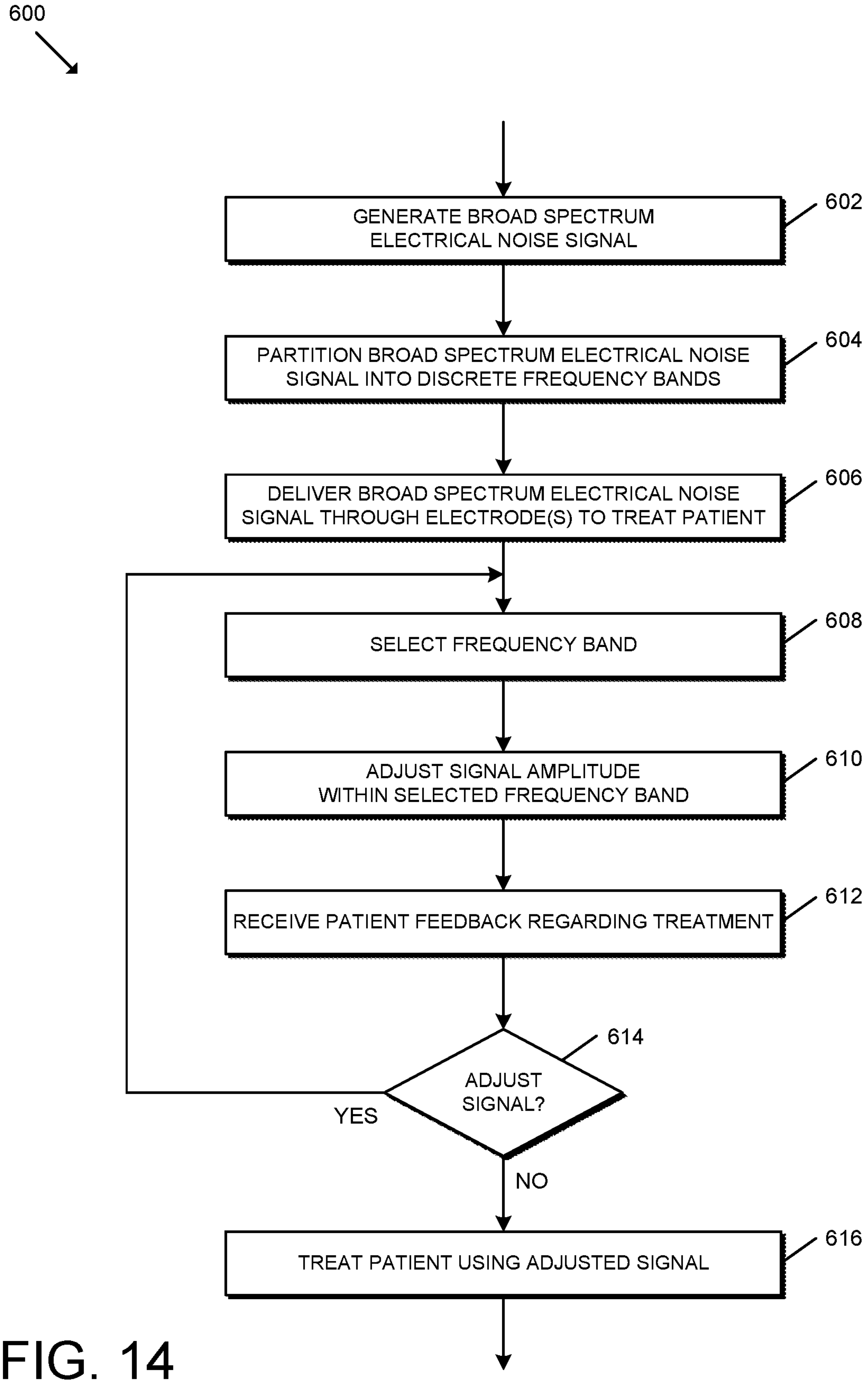
FIG. 14 is a simplified flow diagram of at least one embodiment of a method for providing therapy to a patient via the application of one or more tunable noise signals.

Referring now to FIG. 14, in use, the tunable noise system 400 may execute a method 600 for providing therapy to a patient via the application of one or more tunable noise signals. It should be appreciated that the particular blocks of the method 600 are illustrated by way of example, and such blocks may be combined or divided, added or removed, and/or reordered in whole or in part depending on the particular embodiment, unless stated to the contrary. The illustrative method 600 begins with block 602 in which the tunable noise system 400 or, more specifically, the noise generator 109 generates a broad spectrum electrical noise signal as described herein (e.g., in response to instructions from the controller 110). For example, in some embodiments, a signal similar to the broad spectrum electrical noise signal of FIG. 15 may be generated (e.g., with white noise below 20 kHz). In block 604, the tunable noise system 400 (e.g., the controller 110) partitions the broad spectrum electrical noise signal into discrete frequency bands. For example, in the example embodiment of FIG. 16, the broad spectrum electrical noise signal of FIG. 15 is partitioned/divided into 31 discrete tunable frequency bandwidths. It should be appreciated that the size of the bandwidths may differ depending on the particular embodiment. Further, although each of the bandwidths are described herein and depicted in FIG. 16 as having the same width, it should be appreciated that one or more of the partitioned frequency bandwidths may have a different width from others in other embodiments. For example, in an embodiment, the frequencies range may be from 0 to 100,000 Hz in equally spaced linear frequency bands (e.g., 2,500 Hz). In an embodiment, each of the frequency bands in a frequency range of 0 Hz to 100 kHz of the partitioned electrical noise signal has a bandwidth of one of 1 kHz or 2 k Hz. In another embodiment, the frequency may be described on a logarithmic scale and described by base2 (e.g., octaves: 10 Hz, 20 Hz, 40 Hz, 80 Hz, 160 Hz, 320 Hz, 640 Hz, 1280 Hz, 2560 Hz, etc.) and/or base-10 (e.g., 10 Hz, 100 Hz, 1,000 Hz, 10,000 Hz, 100,000 Hz, etc.) axis, with bandwidths described a Q-factor (center frequency/bandwidth) or bandwidth: octaves (1⁄10 to 10 oct).

In block 606, the tunable noise system 400 (e.g., the noise generator 109) delivers the broad spectrum electrical noise signal through one or more electrodes 107 to the patient in order to treat the patient. In block 608, the tunable noise system 400 selects a particular frequency band of the discretely partitioned frequency bands for adjustment. In block 610, the tunable noise system 400 adjusts the amplitude of the voltage and/or current of the signal within the selected frequency band, for example, by amplifying the voltage and/or current of the signal within that particular frequency band or attenuating the voltage and/or current of the signal within that particular frequency band. It should be appreciated that the amount of amplification/attenuation of the signal may be user-controlled, predefined, and/or otherwise determined depending on the particular embodiment. It should be appreciated that, in the illustrative embodiment, the clinician and/or patient may select and/or adjust the frequency band using one or more user interface 112 devices. However, the frequency band may be otherwise selected in other embodiments.

As described above, in some embodiments, the tunable noise system 400 may leverage multiple noise generators 109 (or multiple noise signal generators) that generate multiple electrical noise signals to fill the frequency space rather than a single noise generator 109 (or noise signal generator) that generates a single electrical noise signal that is partitioned. For example, instead of using a single noise generator 109 and 10 frequency bands of 2 kHz each, the tunable noise system 400 may use 10 noise generators 109 with each attached to one frequency band with a 2 kHz bandwidth, and collectively "line up" the frequency bands to make up the full 20 kHz frequency space. In such embodiments, selection of a particular frequency band may involve selection of one of the multiple noise generators 109 (or noise signal generators) for adjustment of its corresponding electrical noise signal.

In block 612, the tunable noise system 400 and/or the clinician receives feedback regarding the treatment from the patient. As described above, it should be appreciated that the feedback can be provided by the patient, for example, based on self-report (e.g., introspection, observations of unwanted sensory- and/or motor activity, autonomic dysfunction, etc.), determined from data generated by sensors measuring physiological outcomes, based on data from artificial intelligence or machine learning systems (e.g., output or feedback data), or based on combinations thereof. In block 614, the tunable noise system 400 and/or the clinician determines whether to further adjust the signal applied to the patient based on the patient feedback (e.g., in an effort to most optimally alleviate the patient's condition). If so, the method 600 returns to block 608 in which the tunable noise system 400 selects a frequency band for further adjustment (e.g., the same frequency band for further modification, or a different frequency band for modification). If not, the method 600 advances to block 616 in which the patient is further treated using the adjusted signal, which was tuned for optimal (or improvement) treatment of the patient's condition.

Figure 17:
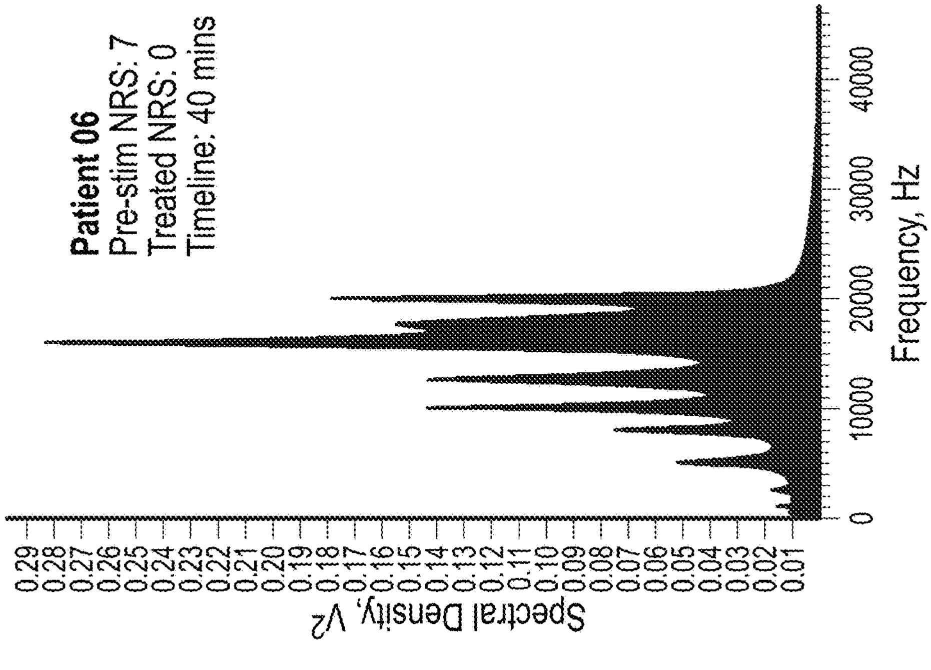
FIGS. 17-19 are graphs of the power spectrum for the broad spectrum electrical noise signal of FIG. 15 after having been tuned to optimally treat three particular patients with intractable leg and back pain using dorsal column stimulation.
Figure 18:
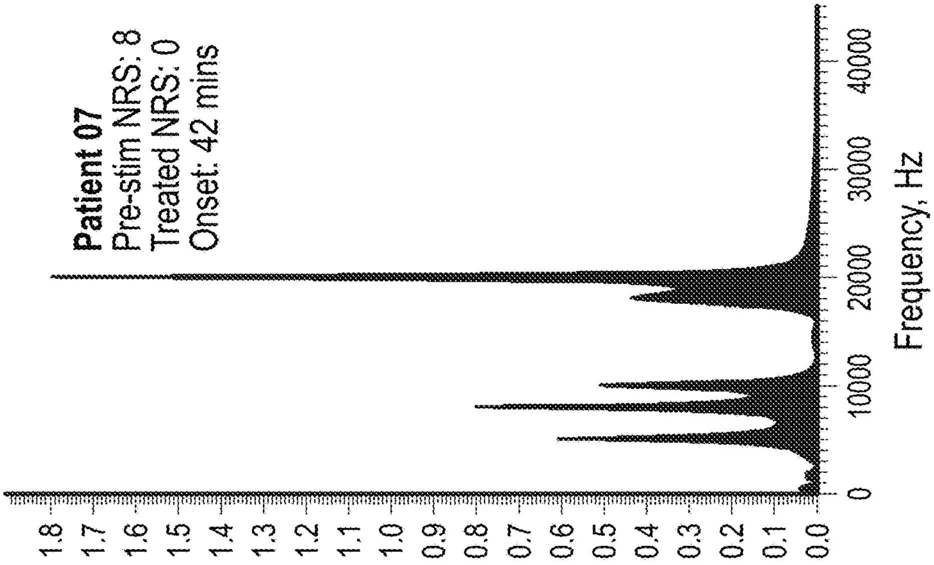
Figure 19:
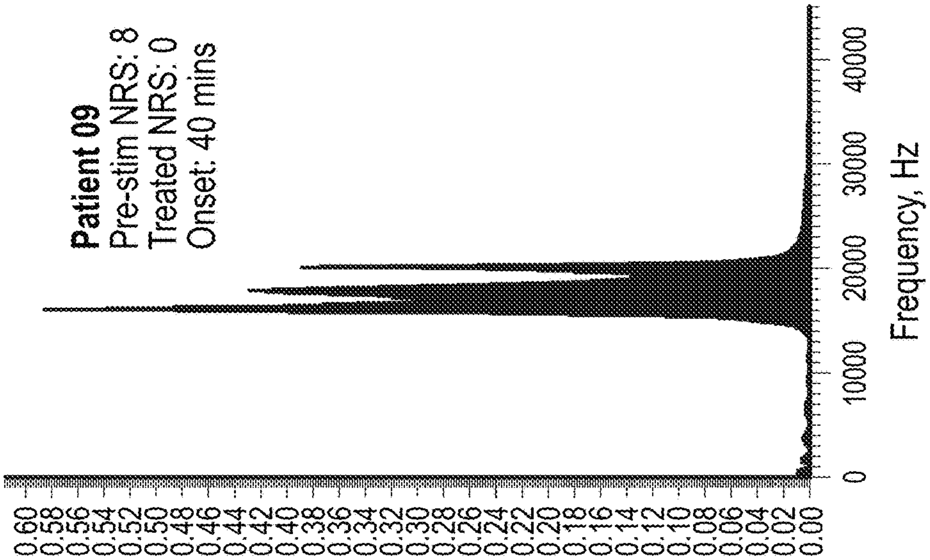
Figure 20:
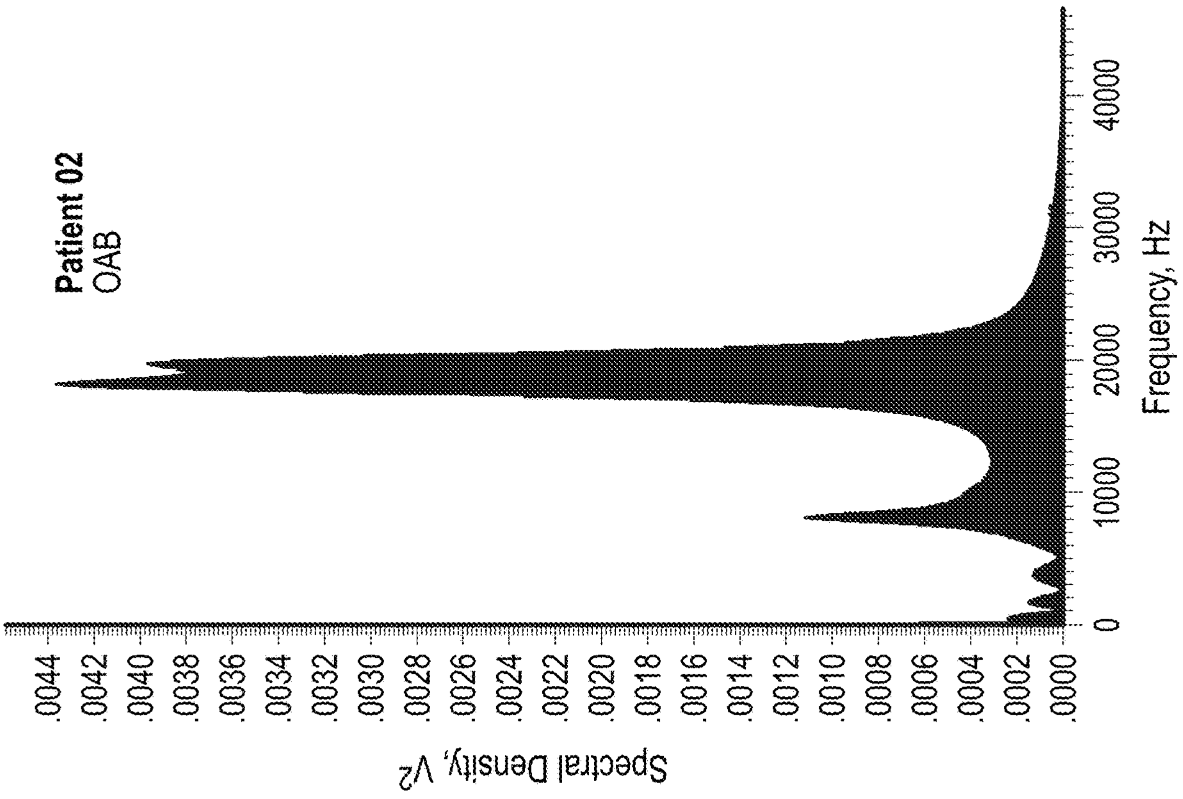
FIG. 20 is a graph of the power spectrum for the broad spectrum electrical noise signal of FIG. 15 after having been tuned to optimally treat a particular patient for overactive bladder (OAB) using sacral nerve stimulation.

It should be appreciated that each patient benefits from a broad spectrum electrical noise signal uniquely tuned specifically to the patient based on the patient's feedback. Accordingly, as described in further detail in reference to the example studies outlined below, FIGS. 17-19 illustrate graphs of the power spectrum for the broad spectrum electrical noise signal of FIG. 15 after having been tuned based on patient feedback to optimally treat three different patients with intractable leg and back pain using dorsal column stimulation. As depicted, although the same treatment was applied, each patient most benefits from a vastly different tuned signal from the other patients. Similarly, FIG. 20 illustrates a graph of the power spectrum for the broad spectrum electrical noise signal of FIG. 15 after having been tuned based on patient feedback to optimally treat a particular patient for overactive bladder using sacral nerve stimulation. The power spectrum of the tuned electrical noise signals shown herein (see, for example, FIGS. 17-20) have multiple local maxima. These local maxima are either neighboring each other or are separated by one or more frequency bands. During tuning, it became evident that local maximum often interacted with each other. That is, two local maxima at optimal frequencies led to largest therapeutic benefit, while a single local maximum or two local maxima delivered at sub-optimal frequencies caused less therapeutic benefit and required larger stimulation power.

Figure 21:
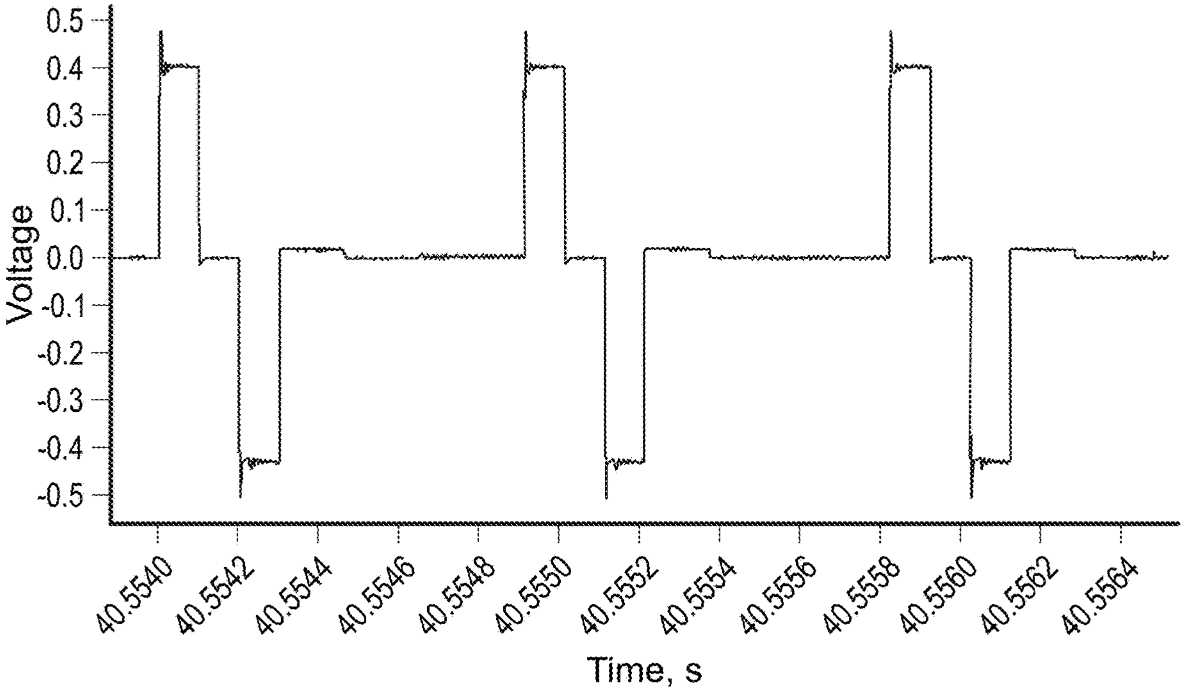
FIG. 21 is a graph of a high-frequency pulse waveform.
Figure 22:
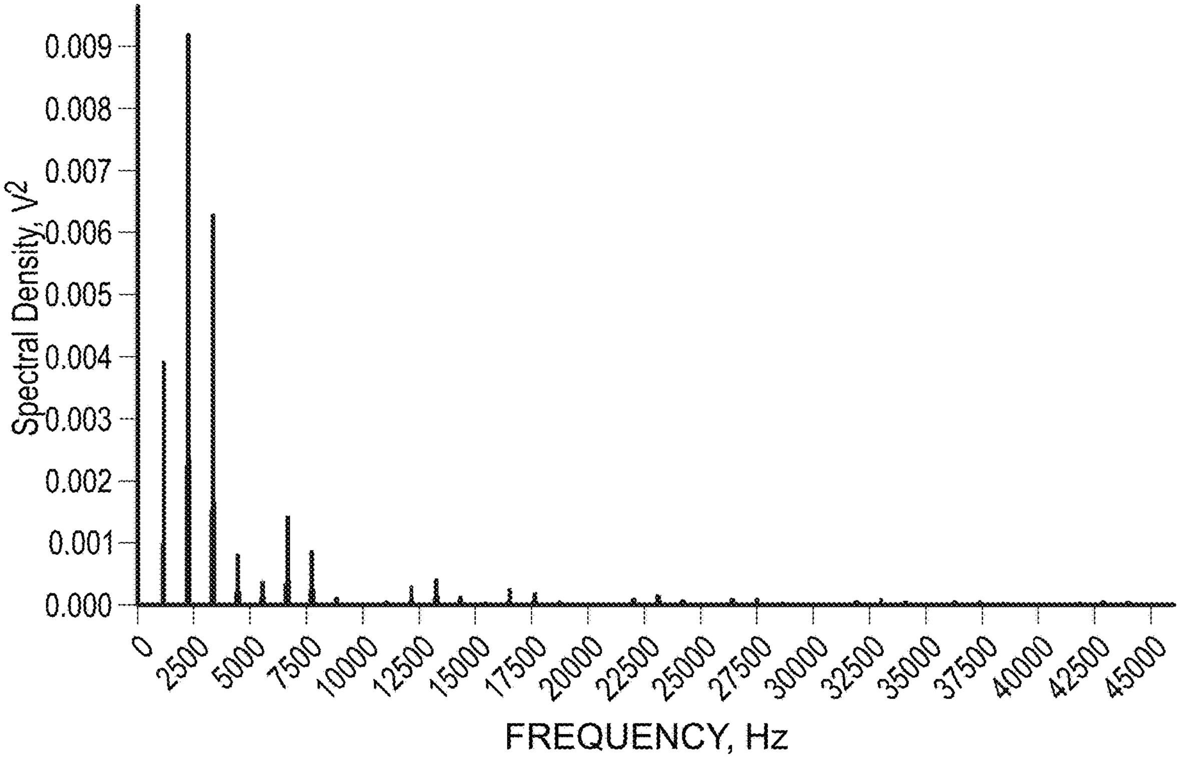
FIG. 22 is a graph of the power spectrum of a high-frequency pulse waveform used to treat a patient.

In contrast to the broad spectrum electrical noise signal described herein, FIG. 21 illustrate a high-frequency pulse waveform generated by a commercially available spinal cord stimulation system, and FIG. 22 illustrates the power spectrum of a high-frequency pulse waveform used to treat a patient. It should be appreciated that this stimulation waveform does not deliver energy at frequencies that are less than the fundamental frequency (1100 Hz) or between harmonics, and the energy content delivered in each harmonic is fixed to that of the fundamental frequency and cannot be independently modulated.

It should be appreciated that the technologies described herein have revealed substantial patient benefits in various experimental studies. For example, one example study involved the tuned electrical noise stimulation of the spinal cord in persons with intractable leg and back pain. In that study, electrical noise stimulation was delivered to patients (n=20) with intractable leg and back pain. The stimulation was delivered to the long axons of the dorsal columns in the spinal cord and to nearby glial cells (not mechanoreceptors). Intractable leg and back pain have central origins and are not dependent on external stimuli. It should be appreciated that noise stimulation does not simply reduce the action potential threshold needed for a stimulus applied to the sensory receptors to fire an action potential.

All study participants were candidates for spinal cord stimulation (SCS) and were trialed using a commercially available stimulation system (e.g., to compare pulse-based waveforms to the tunable noise technologies described herein). After a 24-hour washout period, a purpose-build electrical stimulator was connected to the implanted lead (8-electrical contacts, cylindrical) that was used previously for trialing. As such, electrical noise stimulation (0≤20 kHz; ≤50 mA; ≤160 V) was delivered to the long axons of the dorsal spinal cord and to the nearby non-neural glial cells. Patients were assigned to one of two groups for testing (Groups A & B). Patients (n=15) participating in Group A of the study received white noise electrical stimulation and adjusted the amplitude of the entire noise envelope as necessary to best reduce their pain. Patients (n=10) participating in Group B of the study also received white noise electrical stimulation but further tuned the power of ten independent frequency bands that composed the full spectrum of the white noise signal (0-20 kHz) to maximize pain reduction. That is, the stimulation delivered to persons in Group B was tuned by amplifying or attenuating the power within individual bandwidths and/or combinations of bandwidths until the patient reported a maximal reduction in pain. During tuning, each patient was instructed to remain in a stationary (i.e., resting) position that was comfortable for the patient. Once the electrical noise stimulation was tuned, the patient was allowed to move around (sit-to stand, ambulate, etc.) to better assess activity-related sensations. Participants verbally reported the intensity of their pain (using the Numerical Pain Rating Scale; 11-point scale), the sensations elicited by the stimulation, and their satisfaction with the treatment (using the Likert Scale).

The results of this example study were exceptional. Electrical noise stimulation delivered to the dorsal spinal cord reduced intractable leg and back pain in all patients tested. Moreover, all electrical noise stimulation was well tolerated, and the quality and satisfaction of pain relief were excellent. No adverse events were reported.

Persons participating in Group A reported an average of 70% reduction in pain (Pre-treatment: 6.5±1.2; Post-treatment: 4.5±1 NRS) after 3 hours of continuous stimulation. Two of these patients preferred supra-sensory threshold stimulation intensities, which was felt as "a wobble" sensation that occurred randomly.

Persons in Group B reported a 98% reduction in pain (Pre-treatment: 6.1±0.9; Post-treatment: 0.1±0.4 NRS) after only 45 minutes of receiving tuned electrical noise stimulation. Moreover, the power spectrums describing the tuned stimulation waveforms for optimal pain relief demonstrated multiple local maxima, which were unique to each patient (see FIGS. 17-19). The local maxima were separated by empty frequency bands in some trials, and neighbored other local maxima in other trials. Moreover, it was observed that patients, who were stationary, would tune their noise settings several times during the first hour of stimulation, then would seldom tune again during the hours afterwards. All patients participating in Group B preferred sub-sensory threshold intensities and described the treatment as simply "erasing" the pain.

Lastly, in comparison, the pulsed-based stimulation system reduced the average pain score by 30% (Pre-treatment: 6.23±2.12; Post-treatment: 4.38±3.00 NRS), and 7 of 20 patients, who had a 50% pain reduction or greater, converted (per clinical care) to an implantable stimulation system. Pulse-based stimulation was delivered at intensities sufficient to maximize pain-reduction, and all patients reported feeling sensations consistent with "electrical paresthesia" during their trial. Only one patient preferred the "buzzing" sensation elicited by the stimulation, noting that it assured her that the device was active. All patients indicated that the tunable noise stimulation system was preferable compared to the pulse-based commercial SCS system trialed prior to testing, because of the magnitude of pain reduction and sensations elicited during treatment.

According, the technologies described herein are improvements in that tuned electrical noise stimulation of the spinal cord effectively and comfortably treats intractable leg and back pain and is preferred to a commercially available pulse-based stimulation therapy.

Tuned electrical noise stimulation was more effective at reducing pain than the un-tuned noise treatment, and both were more effective than the pulsed-based stimulation therapy. Moreover, patients in Group B, who could tune their own therapy, achieved greatest pain relief with stimulation delivered at intensities and frequencies that did not cause sensory perception. Incidentally, the intensity and frequency combinations produced by the tunable noise system could not be delivered to the patient via the pulse-based system. Patients participating in Group A were more likely to find greatest pain relief at intensities closer to sensory-threshold, and all pulse-based treatments were felt as a buzzing sensation (supra-threshold). These findings suggest that the flexibility in frequency and power inherent to the tunable electrical noise stimulation system allows the user to customize their therapy without having to overstimulate non-targeted tissues (causing electrical paresthesia and discomfort) or under stimulate targeted tissues necessary to completely mitigate their pain. Moreover, the flexibility of the tunable electrical noise system was also demonstrated by a decreased variability in pain score between and within patients compared to the un-tuned noise system and pulse-based therapy. Lastly, the tuned electrical noise stimulation system reduced pain (which is a perception) in real-time during a single experimental session where the patient was stationary, and without the dependence of external sensory stimuli.

Another example study involved the tuned electrical noise stimulation of the sacral nerves in persons with urinary urge incontinence. In that study, tuned electrical noise stimulation was delivered to a sacral nerve in persons with urinary urge incontinence (N=5). All study participants were candidates to receive a sacral nerve stimulation (SNS) device and had been implanted with a commercially available lead (InterStim® Evaluation Lead, Medtronic, Minneapolis MN) at the S2/S3 level for trialing. Prior to electrical noise stimulation, baseline measures were collected: 3-Incontinence Question questionnaire, and a 3-day voiding diary describing fluid intake, volume voided, leakage and urgency. In the clinical setting, the percutaneous trial lead was connected to a purpose-built tunable electrical noise generator for sacral nerve stimulation. A broad spectrum of electrical noise (white noise) was delivered to each patient, covering a frequency ranging from 0 to 40 kHz. The frequency space was split into 9 frequency bands: (1) 1≤2,500 Hz; (2) 2,500≤5,000 Hz; (3) 5,000≤7,500 Hz; (4); 7,500≤10,000 Hz; (5) 10,000≤12,500 Hz; (6) 12,500≤15,000 Hz; (7) 15,000≤17,500 Hz; (8) 17,500≤20,000 Hz, and (9) 20,000 Hz≤40,000 Hz. For each patient, the sensory-threshold was determined individually for each of the 9 frequency bands. That is, the amplitude of each frequency band was increased or decreased until the patient could sense a "wobbling" sensation 50% of the time. Afterwards, all frequency bands were played at an amplitude of 90% of the stimulation amplitude needed to achieve sensory-threshold. Patient's further adjusted the amplitudes of each frequency band until their sensations of urgency had been completely abolished. The final stimulation setting became known as their "tunable noise signature." The tunable noise signature was delivered to all patients for a period of 2.5-3 hours. The outcome measures of the study were the quality (volume voided, sense of urgency, leakage), satisfaction, and tolerability of overactive bladder symptom relief that the patient experienced during electrical noise stimulation. These self-reported measures collected during the experimental trial were compared to the baseline measures.

The results found that electrical noise stimulation delivered to the sacral nerves was well tolerated, with tolerability being ranked as 'Excellent" across all patients tested. Patients did not report any adverse events or any level of discomfort. The patient's overall satisfaction with relief of overactive bladder symptoms was stated as "Excellent" (N=4/5) and "Very Good" (N=1/5). During and immediately after stimulation, the baseline leakage score of 1-2 (leakage ranging from few drops to <30 ml) and urgency score of 2-3 (moderate-to-severe difficulty to postpone) were both reduced to the score of 0. Meanwhile, the single episode volume voided (corrected to fluid intake amount) was increased from 30-40 ml to 65-80 ml. There were no episodes of fecal incontinence associated with electrical noise stimulation. Lastly, the tunable noise signatures collected from the 5 patients were each unique, and sub-sensory threshold (could not be felt by the patient). FIG. 20 shows the power spectrum collected during a single stimulation session for a particular patient.

Preliminary results have demonstrated that tuned electrical noise stimulation of the sacral nerves does not cause patients discomfort and a single stimulation trial is feasible to improve symptoms of urinary urge incontinence by reducing urgency and leakage as well as increasing the voided urine volume in patients.

What is claimed is:

1. A system for providing therapy to a patient, the system comprising:
- at least one electrode;
- at least one noise generator coupled to the at least one electrode; and
- a controller comprising at least one processor and at least memory having a plurality of instructions stored thereon that, in response to execution by the at least one processor, causes the controller to:
  - instruct the at least one noise generator to generate an electrical noise signal;
  - partition the electrical noise signal into a plurality of discrete frequency bands, each of the discrete frequency bands having a corresponding bandwidth;
  - deliver the electrical noise signal through the at least one electrode to the patient to target at least one of neural tissue or non-neural tissue of the patient;
  - adjust an amplitude of one or more of a voltage or current of the electrical noise signal within a selected frequency band of the plurality of discrete frequency bands to generate an adjusted electrical signal based on feedback received from the patient; and
  - deliver the adjusted electrical signal through the at least one electrode to provide therapy to the patient.

2. The system of claim 1, wherein the feedback received from the patient is patient self-report regarding the therapy delivered to the patient.

3. The system of claim 1, further comprising at least one sensor configured to measure one or more physiological outcomes of the patient; and
- wherein the feedback is based on data generated by the at least one sensor.

4. The system of claim 1, wherein the feedback comprises data received from a machine learning system.

5. The system of claim 1, wherein to adjust the amplitude of one or more of the voltage or current of the electrical noise signal within the selected frequency band of the plurality of discrete frequency bands comprises to adjust the amplitude of the voltage of the electrical noise signal within the selected frequency band of the plurality of discrete frequency bands.

6. The system of claim 5, wherein the amplitude of the voltage of the electrical noise signal within the selected frequency band of the plurality of discrete frequency bands is adjustable within a range of 0.01 V to 200 V.

7. The system of claim 5, wherein the amplitude of the voltage of the electrical noise signal within the selected frequency band of the plurality of discrete frequency bands is adjustable within a range of 0.1 V to 100 V.

8. The system of claim 5, wherein the amplitude of the voltage of the electrical noise signal within the selected frequency band of the plurality of discrete frequency bands is adjustable within a range of 0.5 V to 50 V.

9. The system of claim 1, wherein to adjust the amplitude of one or more of the voltage or current of the electrical noise signal within the selected frequency band of the plurality of discrete frequency bands comprises to adjust the amplitude of the current of the electrical noise signal within the selected frequency band of the plurality of discrete frequency bands.

10. The system of claim 1, wherein to partition the electrical noise signal into the plurality of discrete frequency bands comprises to partition the entire frequency range of the electrical noise signal into the plurality of discrete frequency bands.

11. The system of claim 1, wherein the at least one noise generator consists of a single noise generator.

12. The system of claim 1, wherein the at least one noise generator comprises a first noise signal generator and a second noise signal generator;

wherein to instruct the at least one noise generator to generate the electrical noise signal comprises to (i) instruct the first noise signal generator to generate a first electrical noise signal within a first frequency band of the plurality of discrete frequency bands and (ii) instruct the second noise signal generator to generate a second electrical noise signal within a second frequency band of the plurality of discrete frequency bands; and wherein the electrical noise signal is compiled from at least the first electrical noise signal and the second electrical noise signal.

13. The system of claim 1, wherein the at least one noise generator is configured to generate the electrical noise signal based on one or more of subtractive synthesis, additive synthesis, component modeling synthesis, wavetable synthesis, vector synthesis, linear arithmetic synthesis, phase distortion synthesis, frequency modulation synthesis, sample-based synthesis, or random number generation.

14. The system of claim 1, wherein to adjust the amplitude of one or more of the voltage or current of the electrical noise signal within the selected frequency band of the plurality of discrete frequency bands comprises to:

adjust an amplitude of one or more of the voltage or current of the electrical noise signal within a first frequency band of the plurality of discrete frequency bands to a first amplitude; and adjust an amplitude of one or more of the voltage or current of the electrical noise signal within a second frequency band of the plurality of discrete frequency bands to a second amplitude different from the first amplitude.

15. The system of claim 1, wherein each of the discrete frequency bands has the same bandwidth.

16. The system of claim 1, wherein each of the discrete frequency bands is an octave band.

17. The system of claim 1, wherein the at least one noise generator comprises a filter bank having a plurality of bandpass filters;

wherein each bandpass filter of the plurality of bandpass filters is associated with a corresponding discrete frequency band of the plurality of discrete frequency bands such that the bandpass filter passes signal frequencies within the corresponding bandwidth; and wherein to partition the electrical noise signal into the plurality of discrete frequency bands comprises to process the electrical noise signal with the filter bank.

18. A system for providing electrical stimulation therapy to a patient, the system comprising:

at least one electrode;

at least one noise generator coupled to the at least one electrode; and a controller comprising at least one processor and at least memory having a plurality of instructions stored thereon that, in response to execution by the at least one processor, causes the controller to:

instruct the at least one noise generator to generate an electrical noise signal;

partition the electrical noise signal into a plurality of discrete frequency bands, each of the discrete frequency bands having a corresponding bandwidth;

deliver the electrical noise signal through the at least one electrode to the patient to target tissue of the patient;

adjust one or more of an amplitude of a voltage of the electrical noise signal, an amplitude of a current of the electrical noise signal, or a phase component of the electrical noise signal within a selected frequency band of the plurality of discrete frequency bands to generate an adjusted electrical signal; and deliver the adjusted electrical signal through the at least one electrode to provide the electrical stimulation therapy to the patient.

19. A system for providing electrical stimulation therapy to a patient, the system comprising:

at least one electrode;

at least one signal generator coupled to the at least one electrode; and a controller comprising at least one processor and at least memory having a plurality of instructions stored thereon that, in response to execution by the at least one processor, causes the controller to:

instruct the at least one signal generator to generate an electrical stimulation signal;

partition the electrical stimulation signal into a plurality of discrete frequency bands, each of the discrete frequency bands having a corresponding bandwidth;

deliver the electrical stimulation signal through the at least one electrode to the patient to target at least one of neural tissue or non-neural tissue of the patient;

adjust, for each of a plurality of selected frequency bands of the plurality of discrete frequency bands, a corresponding amplitude of one or more of a voltage or current of the electrical stimulation signal within a corresponding frequency band of the plurality of discrete frequency bands to generate an adjusted electrical stimulation signal based on feedback received from the patient; and deliver the adjusted electrical signal through the at least one electrode to provide the electrical stimulation therapy to the patient.

20. The system of claim 19, wherein to adjust, for each of the plurality of selected frequency bands of the plurality of discrete frequency bands, the corresponding amplitude of one or more of the voltage or current of the electrical stimulation signal within the corresponding frequency band of the plurality of discrete frequency bands comprises to:

adjust an amplitude of one or more of the voltage or current of the electrical stimulation signal within a first frequency band of the plurality of discrete frequency bands based on first feedback received from the patient to generate a first adjusted electrical stimulation signal; and adjust an amplitude of one or more of the voltage or current of the first adjusted electrical stimulation signal within the second frequency band of the plurality of discrete frequency bands based on second feedback received from the patient to generate a second adjusted electrical stimulation signal.

* * * * *